US009428559B2

(12) United States Patent
Abbas et al.

(10) Patent No.: US 9,428,559 B2
(45) Date of Patent: Aug. 30, 2016

(54) GENES CONFERRING TOLERANCE TO ETHANOL AND HIGH TEMPERATURE FOR YEASTS

(71) Applicant: ARCHER DANIELS MIDLAND COMPANY, Decatur, IL (US)

(72) Inventors: Charles Abbas, Champaign, IL (US); Andriy Sibirny, Lviv (UA); Andriy Voronovsky, Lviv (UA); Olena Ishchuk, Lviv (UA)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 14/358,876

(22) PCT Filed: Jan. 11, 2013

(86) PCT No.: PCT/US2013/021100
§ 371 (c)(1),
(2) Date: May 16, 2014

(87) PCT Pub. No.: WO2013/106617
PCT Pub. Date: Jul. 18, 2013

(65) Prior Publication Data
US 2014/0356879 A1   Dec. 4, 2014

Related U.S. Application Data

(60) Provisional application No. 61/585,917, filed on Jan. 12, 2012, provisional application No. 61/585,873, filed on Jan. 12, 2012.

(51) Int. Cl.
*C12N 15/81* (2006.01)
*C07K 14/39* (2006.01)
*C12P 7/06* (2006.01)
*C12Q 1/68* (2006.01)

(52) U.S. Cl.
CPC .............. *C07K 14/39* (2013.01); *C12N 15/81* (2013.01); *C12N 15/815* (2013.01); *C12P 7/06* (2013.01); *C12Q 1/6811* (2013.01); *Y02E 50/17* (2013.01)

(58) Field of Classification Search
None
See application file for complete search history.

(56) References Cited

U.S. PATENT DOCUMENTS

| 8,071,298 | B2 * | 12/2011 | Abbas ............... | C12N 9/88 435/254.2 |
| 8,323,952 | B2 * | 12/2012 | Abbas ............... | C07K 14/39 435/254.2 |
| 8,507,217 | B2 * | 8/2013 | Dmytruk ............ | C12P 7/06 435/15 |
| 2013/0084616 | A1 * | 4/2013 | Abbas ............... | C07K 14/39 435/161 |
| 2014/0356879 | A1 * | 12/2014 | Abbas ............... | C12P 7/06 435/6.15 |

FOREIGN PATENT DOCUMENTS

| EP | 1258493 A1 * | 11/2002 |
| EP | 1258494 A1 * | 11/2002 |
| EP | 1338608 A2 * | 8/2003 |

OTHER PUBLICATIONS

Hu et al, "Approaching a complete repository of sequence-verified protein-encoding clones for *Saccharomyces cerevisiae*", Genome Res. 17 (4), 536-543 (2007).*
Alper et al, Science, Dec. 2006. 314:1565-1568.*
Hu et al, Genetics, Mar. 2007, 175:1479-1487.*
Brachmann et al., Designer strains derived from *Saccharomyces cerevisiae* S288C: useful set of strains and plasmids for PCR-mediated gene disruption and other applications, Yeast, vol. 14: 115-132(1998), John Hopkins University School of Medicine MD, USA.
Brodsky et al., Pre-mRNA processing factors are required for nuclear xport, RNA, pp. 1737-1749, 2000, USA.
Faber et al., Highly-efficient electrotransformation of the yeast *Hansenula polymorpha*, Current Genetics, Aug. 1993, pp. 25:305-310, USA.
Gellissen et al., Heterologous protein production in methylotrophic yeasts, Appl. Microbiol. Biotechnol, pp. 54:741-450, May 2000, USA.
Gleeson et al., Genetic analysis in the methylotrophic yeast *Hansenula polymorpha*, Yeast, University of Sheffield, vol. 4: 293-303, Apr. 1998.
Guerra et al., Hypoxia abolishes transience of the heat-shock response in the methylotrophic yeast *Hansenula polymorpha*, Microbiology, vol. 151: 805-811, 2005.

(Continued)

*Primary Examiner* — Nita M Minnifield
(74) *Attorney, Agent, or Firm* — Corey Crafton

(57) ABSTRACT

Methods of identifying genes conferring ethanol tolerance in yeasts, genes that confer ethanol tolerance, and mutant strains used to identify such genes are described. A gene herein designated HpETT1 was isolated from the yeast *Hansenula polymorpha*. Expression of HpETT1 in an ethanol sensitive mutant *H. polymorpha* strain designated 7E complimented ethanol sensitivity of the mutant. When multiple copies of the HpETT1 were integrated into the genome and overexpressed, the transformed strain demonstrated approximately 10-fold greater resistance to ethanol and resistance to the protein misfolding agent AZC. Expression of HpETT1 also increased ethanol tolerance in *Saccharomyces cerevisiae*. HpEtt1 has 39% sequence identity to a previously identified protein from *S. cerevisiae* denoted MPE1, however, the MPE1 gene does not confer ethanol resistance to the 7E mutant. Another gene from the yeast *Pichia stipitis* was identified that encodes an orthologue protein having 37% identity to HpETT1 herein designated PsETT1 and also confers ethanol resistance to the 7E mutant.

5 Claims, 14 Drawing Sheets

(56) References Cited

OTHER PUBLICATIONS

Ishchuk et al., Overexpression of pyruvate decarboxylase in the yeast *Hansenula polymorpha* results in increased ethanol yield in high-temperature fermentation of xylose, FEMS Yeast Res, pp. 1164-1174 2008.

Jensen et al., A block to mRNA nuclear export in S. cerevisiae leads to hyperadenylation of transcripts that accumulate at the site of transcription, Molecular Cell, vol. 7, pp. 887-898, Apr. 2001.

Krebber et al., Uncoupling of hnRNP Npl3p from mRNAs during the stress-induced block in mRNA export, Genes & Develpment 1999, vol. 13 pp. 1994-2004.

Lane et al., Effect of the proline analogue azetidine-2-carboxylic acid on collagen synthesis in vivo. I. Arrest of collagen accumulation in growing chick embryos, Biochim. Biophy. Acta, 236 (1971) 517-527.

Lahtchev et al., Isolation and properties of genetically defined strains of the methylotrophic yeast *Hansenula polymorpha* CBS4732, Arch Microbial, (2002) 177: 150-158.

Ryabova et al., Xylose and cellobiose fermentation to ethanol by the thermotelerant methylotropic yeast *Hansenula polymorpha*, FEMS Yeast Research, 4 (2003) 157-164.

Saavedra et al., Regulation of mRNA export in response to stress in *Saccharomyces cerevisiae*, Genes & Development, 1996, vol. 10: 1608-1620.

Siverio et al., Biochemistry and genetics of nitrate assimilation. in . Gellissen (ed.), Hansenula polymorpha—Biology and Applications, 2002 Wiley-VCH, pp. 21-40.

Sohn et al., A dominant selection system designed for copynumber-controlled gene integration in Hansenula polymorpha DL-1. Appl, Microbiol. Biotechnol, (1999) 51: 800-807.

Suckow et al., The expression platform based on H. polymorpha strain RB11 and its derivatives—history,status and perspectives. In G. Gellissen (ed.), Hansenula polymorpha—Biology and Applications, Wiley-VCH, Weinheim, pp. 105-123.

Tani et al., Nuclear accumulation of poly (A)+ RNA in heat-shocked yeast cells: implication of nucleolar involvement in mRNA transport, The American Society for Cell Biology, 1996, pp. 173-192.

Trotter et al., Misfolded proteins are competent to mediate a subset of the responses to heat shock in *Saccharomyces cerevisiae*, J Biol Chem, 277 (47): 44817-44825, 2002.

Ubiyvovk et al., Role of gamma-glutamyltranspeptidase in detoxification of xenobiotics in the yeasts *Hansenula polymorpha* and *Saccharomyces cerevisiae*, Cell Biology International, (2006) 665-671.

Le Thuy Anh Vo et al., Mpe1, a zinc knuckle protein, is an essential component of yeast cleavage and polyadenylation factor required for the cleavage and polyadenylation of mRNA, Molecular and Cellular Biology, Dec. 2001, pp. 8346-8356, vol. 21, No. 24.

Voronovsky et al., Development of a transformation system for the flavinogenic yeast *Candida famata*, FEMS Yeast Research 2, (2002) 381-388.

Yang et al., High-efficiency transformation of Pichia stipitis based on its URA3 gene and a homologous autonomous replication sequence, ARS2, Applied and Environmental Microbiology, 1994, 60(12):4245-4254.

Zagari et al., The effect of the L-azetidine-2-carboxylic acid residue on protein conformation. I. Conformations of the residue and of dipeptides, Biopolymers, vol. 30, 951-959 (1990).

\* cited by examiner

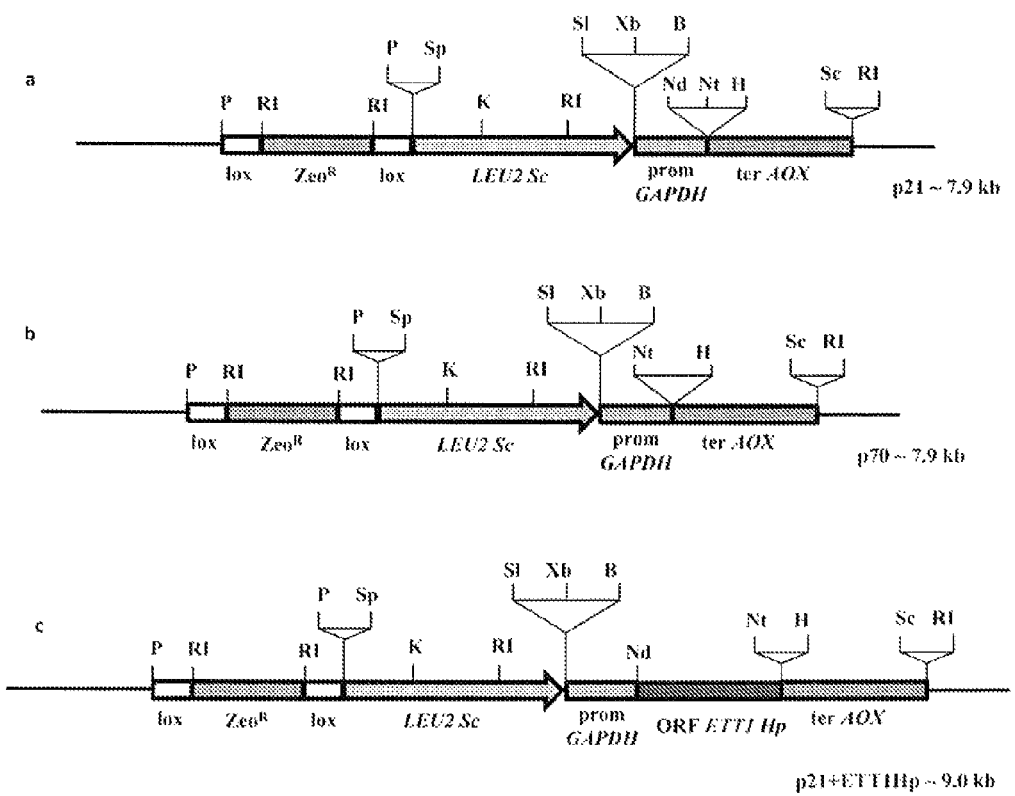
Figure 1.1

Figure 1.2
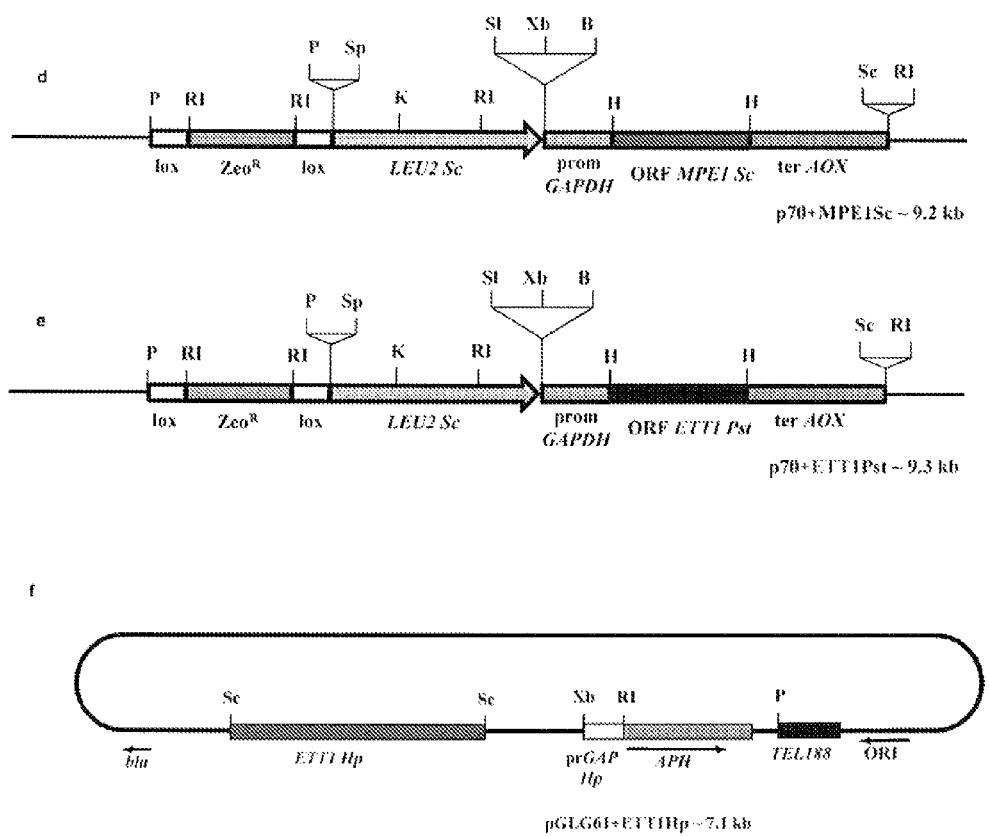

Figure 4

GENES CONFERRING TOLERANCE TO ETHANOL AND HIGH TEMPERATURE FOR YEASTS

CROSS REFERENCE TO RELATED APPLICATIONS

This application is a 35 U.S.C. §371 national phase entry of PCT application No. PCT/US13/02110 filed Jan. 11, 2013, which claims priority to U.S. provisional application Nos. 61/585,873 and 61/585,917, filed Jan. 12, 2012.

TECHNICAL FIELD

The disclosure relates to genes that confer ethanol tolerance to yeasts used to produce ethanol by fermentation, in particular to increased ethanol tolerance of xylose fermenting strains of *H. polymorpha*, to ethanol sensitive mutants of *H. polymorpha* useful to identify ethanol tolerance genes, to ethanol tolerant recombinants of *H. polymorpha*, and more particularly to genetic sequences from *H. polymorpha* and *P. stipitis* herein designated HpETT1 and PsETT1, respectively, that are similar in sequence to the MPE1 gene of *S. cerevisiae* but that confer increased ethanol tolerance in yeasts including *H. polymorpha* and *S. cerevisiae*.

BACKGROUND

The references cited in this Background section and in the Description that follows are to provide a better understanding of the invention described herein after, as a resource for materials and methods that may further enable one to practice the methods and/or obtain the compositions later described herein, and as an abbreviation for such methods. Accordingly each reference cited herein is incorporated by reference to the extent the references provide a teaching that aids in the making and using of the invention later claimed. If there is any conflict in the disclosure provided herein and the cited references, the present disclosure controls over the teaching of the cited reference to the extent they conflict. The citation of a reference anywhere herein is not an admission that such a reference is pertinent to, or prior art to the invention claimed hereafter.

*Hansenula polymorpha* is a yeast species of both industrial and scientific importance. This non-conventional thermotolerant methylotrophic yeast is one of the best yeast systems for the production of heterologous proteins (Gellissen, 2000; Gellissen, (ed.), 2002; Suckow and Gellissen, 2002), it serves as a model to study peroxisome function (Van der Klei and Veenhuis, 2002), methanol metabolism, nitrate assimilation (Siverio, 2002) and stress responses (Ubiyvovk et al., 2006). *H. polymorpha* also has potential to be useful in biofuel production by fermentation of lignocellulosic carbon sources because it is able to ferment xylose (Ryabova et al., 2003), and is one of the most thermotolerant of yeast species (Guerra et al., 2005). However *H. polymorpha*'s utility as an organism to produce ethanol by fermentation may be limited because its growth is rather sensitive to ethanol in comparison to other yeasts, such as *S. cerevisiae*.

SUMMARY

The present inventors recognized that to be useful for commercial applications in biofuel production by fermentation, it would be desirable if the tolerance of *H. polymorpha* to ethanol could be improved. The discoveries described herein arose from research that focused on identification of target gene(s) for constructing ethanol tolerant strains of *H. polymorpha*. The inventors created a library collection of insertional mutants of *H. polymorpha*. From the collection of insertional mutants one transfromant (herein designated 7E) was selected that was shown to be highly sensitive to ethanol. From sequencing the insertional cassette in this mutant it was discovered that the insertion disrupted an open reading frame of a gene herein designated HpETT1 (SEQ. ID NO 1) encoding an unknown protein (SEQ. ID NO: 2) correspondingly designated Ett1. By comparing the amino acid sequence of Ett1 to yeast databases, it was discovered that Ett1 shares about 39% sequence identity with a protein of *Saccharomyces cerevisiae* (SEQ. ID NO: 5) encoded by the MPE1 gene (SEQ. ID NO: 6). This gene was reported to be an essential yeast gene that encodes a protein that is necessary for in vitro RNA 3'-end processing and is a subunit of the so-called CPF complex (Vo et al., 2001). The MPE1 gene is apparently essential for *S. cerevisiae* because a *S. cerevisiae* MPE1 deletion mutant is not viable.

In contrast, the *H. polymorpha* mutant 7E identified by the inventors remains viable despite having a disruption in a gene that has close ORF similarity to the *S. cerevisiae* MPE1 gene. Despite its viability on ordinary growth media, as noted above, the 7E mutant is hypersensitive to ethanol. As further demonstrated herein, expression of the undisrupted HpETT1 gene in the 7E mutant successfully complemented the mutant's hypersensitivity to ethanol.

Searching yeast databases revealed another homologous gene, herein designated PsETT1, present in the genome of another xylose fermenting yeast *Pichia stipitis*. The product of PsETT1, PsEtt1, has about 37% amino acid identity to HpEtt1. The inventors isolated and expressed the PsETT1 gene in the *H. polymorpha* 7E mutant and demonstrated that like HpETT1, expression of the the *P. stipitis* gene at least partially complemented the *H. polymorpha* ett1 mutants hypersensitivity to ethanol.

Still further, it is shown that overexpression of the native HpETT1 gene in *H. polymorpha* using a multi-copy integrant constructed such as described herein resulted in a transformed strain of *H. polymorpha* having about a 10-fold increase in tolerance to ethanol relative to the parent strain. More surprisingly still, it is shown that expression of the *H. polymorpha* HpETT1 gene in *S. cerevisiae* also conferred a detectable increase in ethanol tolerance in that yeast.

Accordingly, the present teaching presents several useful new aspects. One aspect is a mutant strain of *H. polymorpha* characterized as being ethanol sensitive and having a mutation that disrupts functional expression of the HpETT1 gene. Another aspect is a method of identifying a gene that confers ethanol tolerance in a yeast strain that includes transforming the *H. polymorpha* ett1 mutant strain with a vector that expresses a candidate nucleic acid, selecting a transformant that complements the ett1 mutant's sensitivity to ethanol, and identifying the sequence of the candidate nucleic acid to identify the gene that confers ethanol tolerance Another aspect is an isolated nucleic add encoding an Ett1 protein, which is characterized as a nucleic acid that when expressed in the ett1 mutant complements the ethanol sensitivity of that mutant. Representative examples of nucleic acids encoding Ett1 proteins are the HpETT1 gene of SEQ. ID NO: 1 that encodes the HpEtt1 protein of SEQ. ID NO:2 and the PsETT1 gene of SEQ. ID NO: 3 that encodes the PsEtt1 protein of SEQ. ID. NO: 4. A related aspect is identification of a new type of protein class designated Ett1 and isolated versions of the same. Still another related aspect is a recombinant nucleic acid comprising a sequence that encodes an Ett1 protein and a promoter that is operable in a selected yeast strain operably configured to express the ETT1 gene in the selected yeast strain. Examples of such vectors are illustrated in FIG. 1 and include p21+ETT1Hp and pGLG61+ETT1Hp each configured to express the *H. polymorpha* Ett1 protein and p70+ETT1Pst that is configured to express a *P. stipitis* Ett1 protein. These vectors have promoters selected to be particularly operable in *H. polymorpha*. Another example is prPGK1Sc+ETT1Hp which are configured to express the HpETT1 gene in *S. cerevisiae*.

Another important aspect is yeast strains having enhanced ethanol tolerance that can be produced by overexpressing an Ett1 protein in the yeast strain. The yeast strain with increased ethanol tolerance can be a *H. polymorpha* strain, a *S. cerevisiae* strain or a *P. stipitis* strain comprising a recombinant nucleic acid that overexpresses at least one of the Ett1 proteins from *H. polymorpha* or *P. stipitis*. Exemplary embodiments of such strains include *H. polymorpha* strains 7E-GAPDHETT1Pst, 7E-GAPDHETT1Hp, and 3Leu+pETT1-10 and *S. cerevisiae* strain BY4742+ prPGK1Sc+ETT1Hp.

It should be noted that initially the nomenclature for the vectors, genes, proteins and strains used in the materials and methods section had the root term "MPE1", followed by a suffix for the organism from which the gene was obtained, i.e., Hp for *H. polymorpha*, Pst for *P. stipitis*, and Sc, for *S. cerevisiae*. This nomenclature was originally used because after searching yeast databases for sequences that were similar to the gene disrupted in the *H. polymorpha* 7E mutant, it was discovered that the closest known sequence was the *S. cerevisiae* MPE1 gene, therefore the closest similar sequences from *P. stipitis* and *H. polymorpha* were originally given the same name. However, it being now discovered that the *S. cerevisiae* MPE1 gene does not complement the ethanol sensitivity of the *H. polymorpha* 7E mutant, while the similar sequences from *H. polymorpha* and *P. stipitis*, do complement the mutation, it is more appropriate to refer to the *H. polymorpha* and *P. stipitis* genes as a new type of ethanol tolerance genes denominated herein with the suffix "ETT1." Accordingly, the vectors initially denominated as p21+MPE1Hp and pGLG61+ MPE1Hp or p70+MPE1Pst were renamed as p21+HpETT1 and pGLG61+HpETT1 and p70+PsETT1. Only the *S. cerevisiae* gene is referred to strictly as MPE1.

BRIEF DESCRIPTION OF THE DRAWINGS

FIGS. 1.1 and 1.2 show schematic representations of vectors described herein. Figures a and b show *H. polymorpha* expression vectors, c, d, and e show the constructs for expressing the *H. polymorpha* HpETT1 gene, the *S. cerevisiae* MPE1 gene, and the *P. stipitis* PsETT1 gene in *H. polymorpha*. FIG. 1.2f shows a vector for multicopy integration of the HpETT1 gene in *H. polymorpha*.

FIG. 4 shows a sequence comparison between the *H. polymorpha* HpEtt1 protein (Hp), *S. cerevisiae* Mpe1 protein (Sc), *P. stipitis* PsEtt1 protein (Ps) and the consensus sequences between them.

DETAILED DESCRIPTION

Definitions

Figure 2:
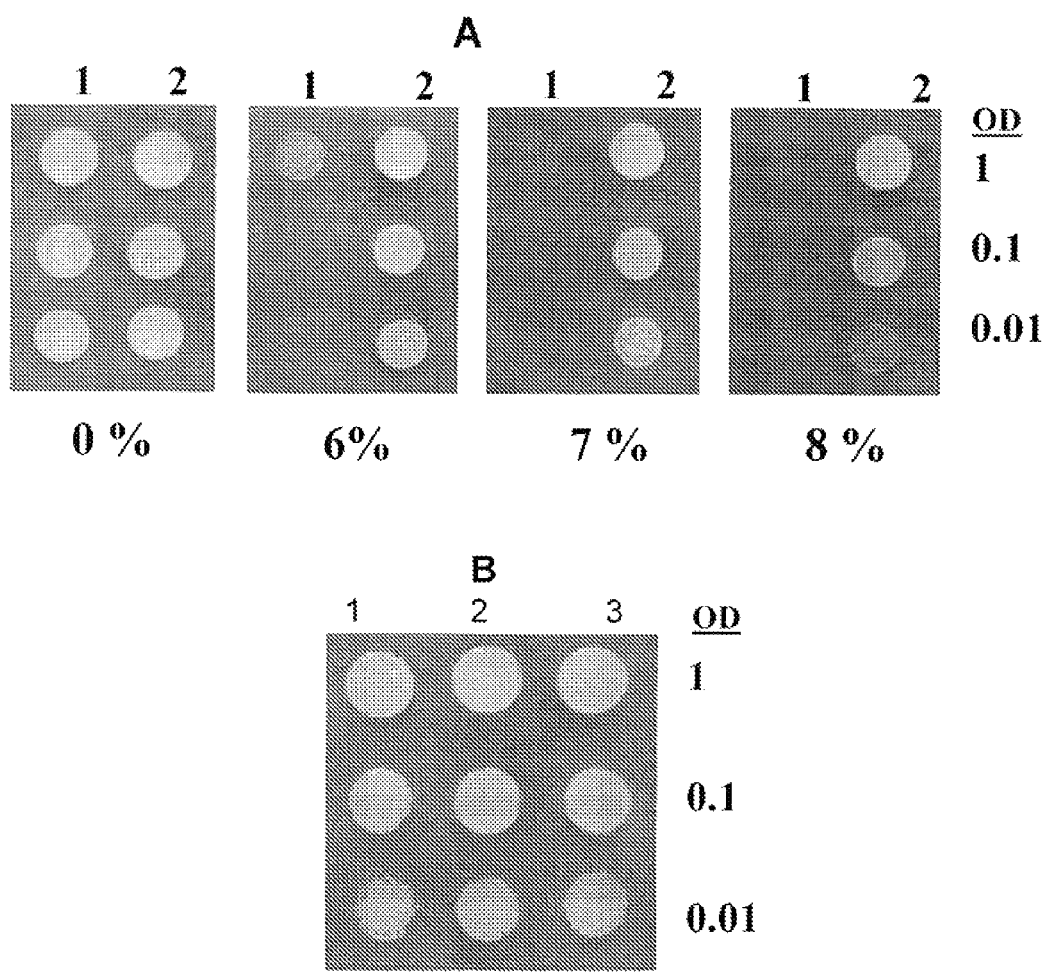
FIG. 2 depicts solid media density assays showing ethanol sensitivity for the HpETT1 mutant *H. polymorpha* strain 7E (1) in comparison to non-mutant strains 3Leu+ (2) and parental strain NCYC495leu1-1 (3). Panel A illustrates the densities after overnight growth at 37° C. of cells initially plated at the indicated optical densities on YNB media plus 2% sucrose with the indicated percentage of ethanol. Panel B illustrates the densities after overnight growth on YNB media in the presence of 1% ethanol.

Certain common or newly introduced terms that have been used herein are believed to be commonly understood to those of ordinary skilled in the art, or would be commonly understood in view of the present disclosure. Such commonly understood meanings are embraced herein, however, to resolve any questions of clarity that may be asserted by use of certain terms, the following non-limiting definitions are provided to assist in better understanding the present invention.

A sibling strain, is one strain of microorganism that is of the same species as another strain although not necessarily of the same genotype.

A parental strain, is a strain of microorganism that has the same genetic background as a derivative strain of the same microorganism, except for alterations that have been made in the derivative strain.

An ett1 mutant strain, is a strain of *H. polymorpha*, exemplified herein by *H. polymorpha* 7E, having a mutation that disrupts the expression of the gene identified herein as HpETT1 and which shows sensitivity to growth on ethanol in comparison to a sibling or parental *H. polymorpha* strain lacking the mutation.

An ETT1 gene is a gene from any source that encodes a protein (Ett1 protein) that when expressed in an ett1 mutant strain, at least partially overcomes the ethanol sensitive growth properties of the mutant strain.

A HpETT1 gene is a nucleic acid obtained from a strain of *H. polymorpha* that encodes an Ett1 protein, exemplified herein by SEQ. ID NO 1 for the gene and SEQ. ID NO 2 for the protein (HpEtt1 protein).

A PsETT1 gene is a nucleic acid obtained from a strain of *P. stipitis* that encodes an Ett1 protein, exemplified herein by SEQ. ID NO 3 for the gene and SEQ. ID NO 4 for the protein (PsEtt1 protein).

Overexpress, means to genetically express a nucleic acid encoding an ORF in a transformed host cell to a greater agree than the same nucleic acid is expressed in a non-transformed parent of the host cell under similar growth conditions.

Increased ethanol sensitivity or ethanol sensitive growth means that that when ethanol is present in a growth medium, a subject strain grows at a slower rate, to a lower density, or otherwise with decreased vigor in comparison to a sibling strain of the same organism grown on the same media.

Enhanced ethanol tolerance means that when ethanol is present in a growth medium, a subject strain grows at a faster rate, to a greater density, or otherwise with increased vigor in comparison to a sibling strain of the same organism grown on the same media.

Materials and Methods Used to Make Exemplary Embodiments

Strains and growth conditions. The yeast strains disclosed herein are listed in Table 1. The *H. polymorpha* NCYC495 leu1-1 strain was used as a recipient for insertional mutagenesis and was maintained on minimal medium containing 0.67% YNB (Difco, Detroit, Mich., USA) supplemented with 2% sucrose and leucine at 40 mg $L^{-1}$ at 37° C. *H. polymorpha* 7E was selected as an insertional mutant of *H. polymorpha* NCYC495 leu1-1 strain that is unable to grow on YPS medium (0.5% yeast extract, 1% peptone and 2% sucrose) supplemented with 7% ethanol.

The *H. polymorpha* CBS4732s strain (Lahtchev et al., 2002) was used as a source of the HpETT1 gene. The strain was maintained on YPD medium (0.5% yeast extract, 1% peptone and 2% glucose) at 37° C.

The *Pichia stipitis* strain CBS6054 (Yang et al., 1994) was used as the source of the *P. stipitis* PsETT1 gene, which is an orthologue of HpETT1. *S. cerevisiae* strain BY4742 (Brachmann et al., 1998) was used as the source for the *S. cerevisiae* MPE1 gene.

The 3Leu+ strain (Ishchuk et al., 2008) was used as a recipient strain for HpFTT1 overexpression in *H. polymorpha*.

Yeast transformants were selected either on YNB medium with 2% sucrose or on YPS medium (0.5% yeast extract, 1% peptone and 2% sucrose) supplemented with geneticin at 1 g $L^{-1}$ or zeocin at 140 mg $L^{-1}$.

The *Escherichia coli* strain DH5α [Φ80dlacZΔM15, recA1, endA1, gyrA96, thi-1, hsdR17 ($r_K^-$, $m_K^+$), supE44, refA1, deoR, Δ(lacZYA-argF) U169] was used in experiments which required a bacterial host. The bacterial strain was grown at 37° C. in the rich (LB) medium as described in Sambrook et al., 1989. Transformed *E. coli* cells were maintained on a medium containing 100 mg $L^{-1}$ of ampicillin.

TABLE 1

Yeast strains used in this study

| Strain | Description | Reference |
| --- | --- | --- |
| H. polymorpha: | | |
| NCYC4895 leu1-1 | leu2 | Gleeson and Sudbery, 1988 |
| 7E | NCYC495 leu1-1 insertional mutant, leucine prototroph | this study |
| CBS4732s | leu2 | Lahtchev et. al., 2002 |
| 3Leu+ | NCYC495 leu1-1 derivative, leucine prototroph | Ishchuk et al., 2008 |
| P. stipitis CBS6054 | wild-type | Yang et al., 1994 |
| S. cerevisiae BY4742 | MATa his3_1 leu2_0 lys2_0 ura3_0 | Brachman et al., 1998 |

Construction of plasmids Two integrative plasmid vectors p21 and p70 (FIG. 1a, FIG. 1b) were constructed for use as the *H. polymorpha* integration and expression cassette. Each plasmid contains the strong *H. polymorpha* constitutive promoter for glyceraldehyde 3-phosphate dehydrogenase gene (GAPDH) and the terminator of alcohol oxidase (AOX). The plasmids p21 and p70 are the derivatives of p19L2 (Voronovsky et al., 2002) and differ only slightly in the restriction sites available for cloning of the subject gene to be expressed.

Based on the initial discovery that the *H. polymorpha* 7E insertional mutant contained an interruption of a gene having an open reading frame with about 39% identity with the *S. cerevisiae* MPE1 gene we sought to obtain the natural *H. polymorpha* homologue of MPE1. The resulting construct was plasmid p21+ETT1Hp (FIG. 1c) which is based on the p21 plasmid cassette (FIG. 1a). The genomic DNA isolated from *H. polymorpha* CBS4732s strain served as a template to obtain the MPE1 homologue herein designated HpETT1, which was obtained by amplification of the genomic DNA containing the open reading frame using the primers IS202 (5'-CGGAATTCCATATGGCTGTCATATACTATA-AGTTC-3') (SEQ. ID NO: 7) and IS203 (5'-TTTATAAT GCGGCCGCTCACTTTTGATTATTGGTCG-3') (SEQ. ID NO: 8). The PCR fragment was treated with restriction endonucleases NdeI and NotI at the underlined restriction sites and cloned into NdeI/NotI-linearized plasmid p21.

The genes homologous to HpETT1 were isolated from *S. cerevisiae* and *P. stipitis* and subcloned into the p70 expression cassette (FIG. 1b) resulting in the constructs p70+ MPE1Sc and p70+ETT1Pst (FIG. 1d, FIG. 1e). The genomic DNA isolated from *S. cerevisiae* BY4742 and *P. stipitis* CBS6054 served as templates to amplify the open reading frames of *S. cerevisiae* MPE1 and PsETT1 genes. For *S. cerevisiae* MPE1 the ORF primer pairs used were: IS249 (5'-CCCAAGCTTATGAGTAGCACGATATTTTAC-3') (SEQ. ID NO: 9) and IS250 (5'-ATC AAGCTTTCATTTCTTAGGGCTTGCGTC-3') (SEQ. ID NO: 10) for *P. stipitis*, the ORF primer pair used were: IS212 (5'-CTCAAGCTTATGTCGTCAGTCGTCTACTATAAG-3') (SEQ. ID NO: 11) and IS213 (5'-GGG AAGCTTCTAATTCTTCTTCTGGTTATTGAC-31 (SEQ. ID NO: 12). The corresponding PCR fragments were treated with endonuclease HindIII at the underlined restriction site and cloned into HindIII-linearized plasmid p70.

Another plasmid for expression of the HpETT1 gene constructed was pGLG61+ETT1Hp (FIG. 1f), which is a derivative of plasmid vector pGLG61 (Sohn et al., 1999). The pGLG61 vector promotes multi-copy-number integration of plasmid tandem repeats into the genome. The *H. polymorpha* HpETT1 gene was amplified from the genomic DNA of *H. polymorpha* CBS4732s strain using primer pair: IS206 (5'-ACGGAGCTCGGTAGATTAGTAAAGGA-AATC-3') (SEQ. ID NO 13) and IS207 (5'-TAT GAGCTCTAGTGATCGTTAAAGGTGACC-3') (SEQ. ID NO: 14). The PCR fragment was treated with restriction endonuclease SacI at the underlined restriction site and ligated with 4.97 kb SacI-fragment of pGLG61.

Molecular biology techniques Plasmid DNA isolations from *E. coli* were carried out by using NucleoSpin® Plasmid QuickPure (Macherey-Nagel, Germany). Taq DNA polymerase and Vent$_R$® DNA polymerase (both New England Biolabs, USA) were used for analytical and preparative PCR, respectively. T4 DNA ligase, T4 DNA polymerase and restriction enzymes were purchased from Fermentas, Lithuania.

Preparations of total DNA from yeast species were carried out by using DNeasy® Tissue Kit (Qiagen, Germany).

Transformation of *H. polymorpha* was performed by electroporation as described previously (Faber et al., 1994).

Southern blotting analysis was performed using the Amersham ECL Direct Nucleic Acid Labelling and Detection System (GE Healthcare, USA).

Recombinant proteins The HpEtt1 protein encoded by the HpETT1 gene of *H. polymorpha* with a sequence of 373 amino acids was expressed as His$_6$fusion peptide after being cloned into pET-32-ac (+) (Novagen). The recombinant polypeptide was produced in *E. coli* BL21(DE3) and purified on nickel-nitriloacetic acid agarose (Qiagen) according to the manufacturer's instructions.

Illustrative Results

Isolation of *H. polymorpha* 7E mutant The parental *H. polymorpha* NCYC495 leu1-1 strain tolerates ethanol concentrations in the medium up to 7-8%. However, insertional mutant 7E was selected among *H. polymorpha* NCYC495 leu1-1 insertional transformants as a one unable to grow on the YNB medium supplemented with 7% ethanol. For this purpose the p19L2 plasmid (Voronovsky et al., 2002) linearized with BamHI was used as an insertional cassette. Leu+ transformants were replica-plated on the ethanol supplemented medium and screened for the growth. Among 200 transformants only one was unable to grow on the 7% ethanol (designated 7E). The 7E mutant proved to be approximately 300-500 times more sensitive to ethanol compared to the control parental strain (3Leu+ transformant) (FIG. 2A). Unlike the recipient strain, the 7E mutant does not tolerate the stress ethanol concentration, but it does grow on the 1% ethanol as a sole carbon source (FIG. 2B) meaning it lacks any defects in ethanol utilization but is sensitive to ethanol concentrations at stress levels.

Figure 3:
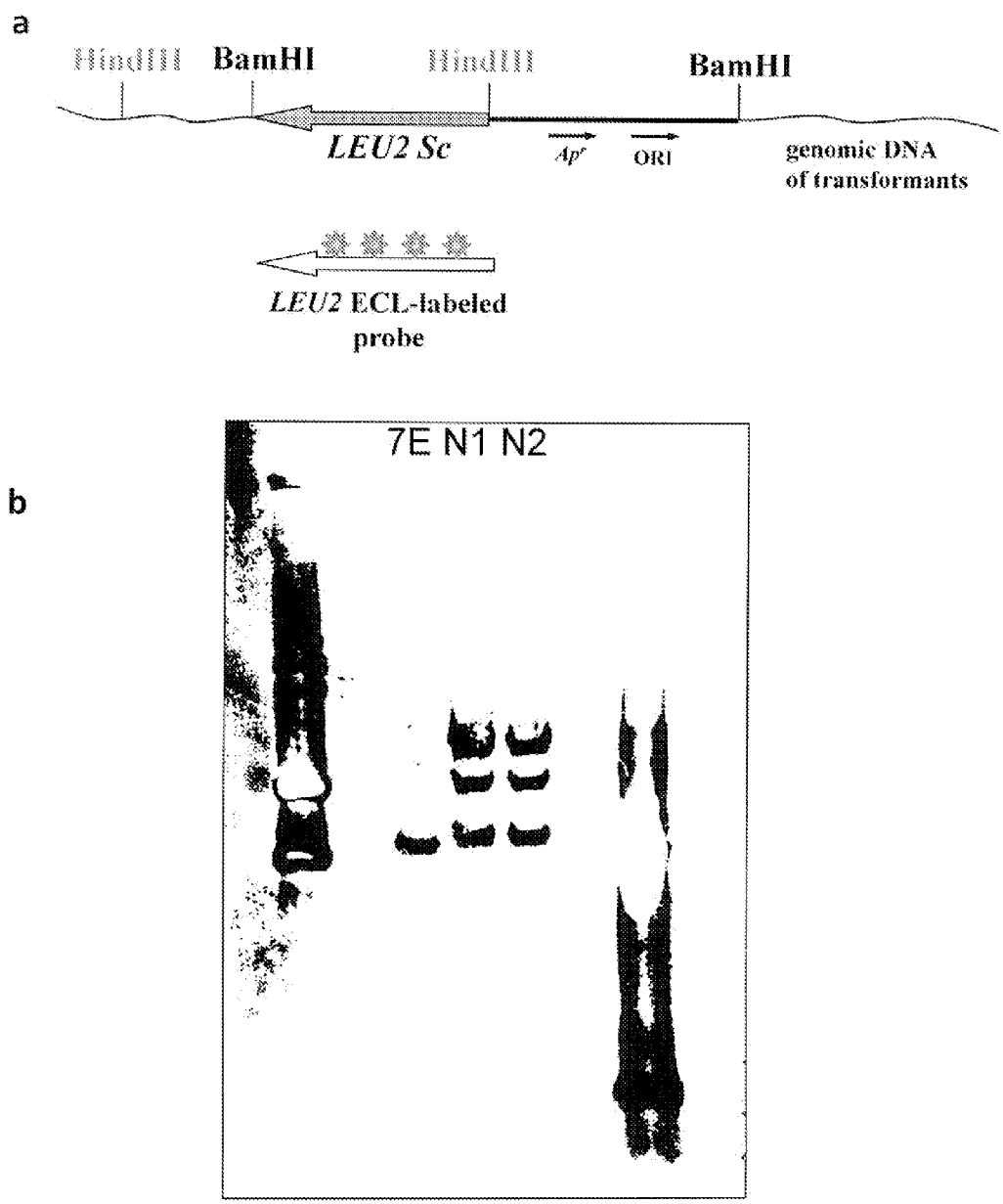
FIG. 3A illustrates a genomic integrant and probe for identification of plasmid chromosomal integrant.
FIG. 3B illustrates a Southern blot for assaying copy number of integrants 7E, N1 and N2.

Plasmid p19L2 carries the LEU2 gene of *S. cerevisiae* and when it is used to transform a *H. polymorpha* strain, 1 to a few copies of the plasmid might be integrated into the genome of *H. polymorpha*. For this reason the copy number of the insertional cassette in the genome of 7E mutant was estimated. The genomic DNA of the 7E mutant and a few other randomly selected Leu$^+$ transformants were treated with HindIII and probed with an ECL-labeled PCR fragment carrying the *S. cerevisiae* LEU2 gene. There is no HindIII site within LEU2 gene so one Southern blotting signal corresponds to one p19L2 copy in the genome (FIG. 3B). It was shown that the 7E mutant carried only one copy of insertional cassette integrated into the genome whereas transformants N1 and N2 gave 3 signals corresponding to 3 plasmids copies being integrated.

Figure 4:
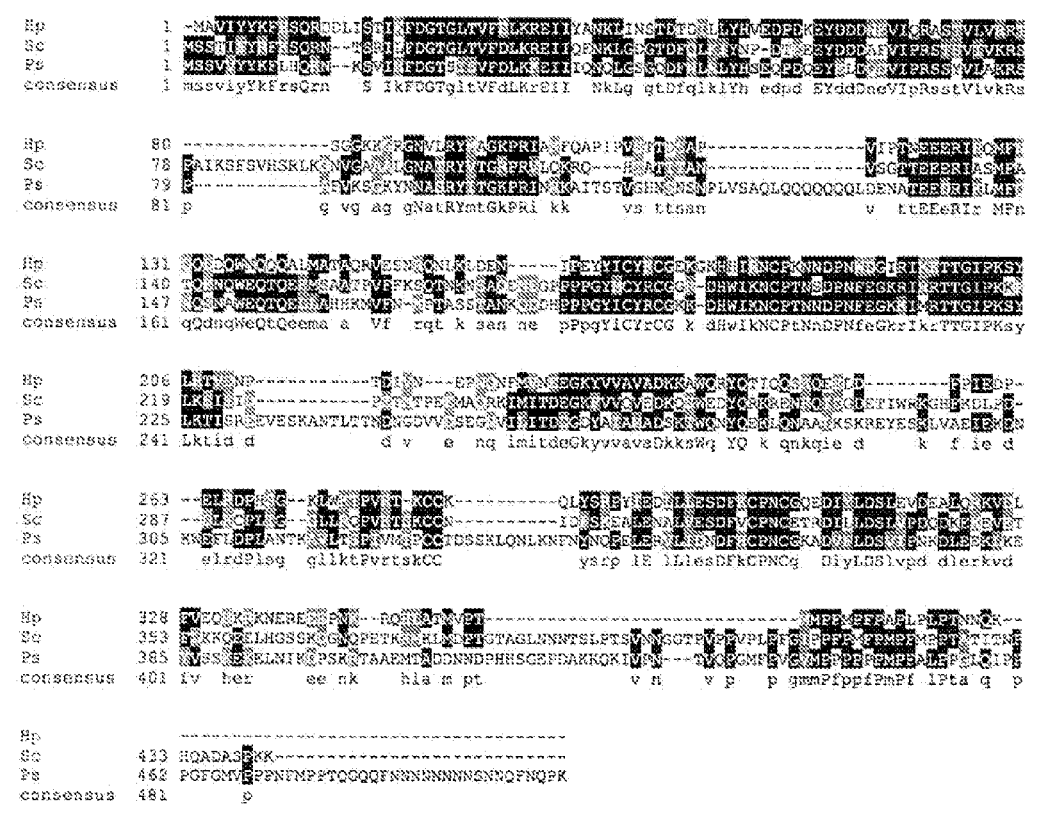

The 7E insertional mutant of *H. polymorpha* has a disrupted gene homologous to the *S. cerevisiae* MPE1 gene The genomic region flanking the insertional cassette in the 7E mutant was sequenced. It was shown that the plasmid disrupted the *H. polymorpha* open reading frame having 39% identity to protein (SEQ. ID NO: 6) encoded by the *S. cerevisiae* MPE1 gene (SEQ. ID NO: 5) which is annotated as coding an essential component of a cleavage and polyadenylation factor required for cleavage and polyadenylation of mRNA (Vo et al., 2001). A sequence comparison (FIG. 4) for sequences similar to the to *S. cerevisiae* MPE1 gene motifs identified by Vo et al., 2001 revealed that the *H. polymorpha* MPE1 like ORF (i.e., the HpETT1 gene) contains a zinc knuckle-like motif ($CX_2CX_5HX_4C$) between amino acids 168 and 182; a cysteine-rich B domain resembling RING finger between amino acids 266 and 319; and a region from amino acids 4 and 79 with high homology to the so called "A domain" identified in the *S. cerevisiae* homologue (FIG. 4). The insertional cassette in the 7E mutant disrupted the *H. polymorpha* HpETT1 gene by integration at a position 671 bp downstream of the start codon.

Figure 5:
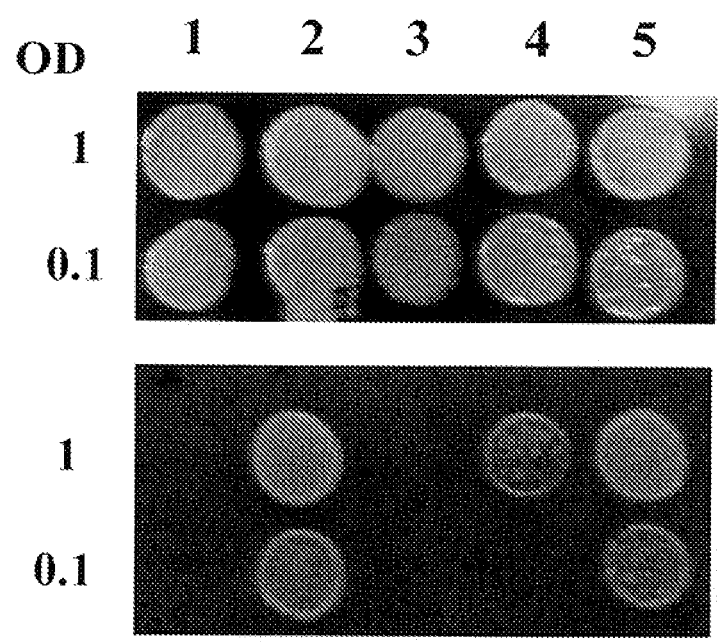
FIG. 5 depicts a solid media density assay showing complementation of the *H. polymorpha* 7E mutation by expression of the HpETT1 and PsETT1 genes but not the *S. cerevisiae* MPE1 gene. The upper panel shows growth on YPD medium alone and the lower panel shows growth on the same plus 7% ethanol. The strains are: (1) the *H. polymorpha* 7E mutant parental strain; (2) the 3Leu+ control; (3) the 7E transformant designated 7E GAPDHMPE1Sc transformed with the *S. cerevisiae* MPE1 gene; (4) the 7E transformant designated 7E-GAPDHETT1Pst transformed with the *P. stipitis* ETT1 gene; and (5) the 7E transformant designated 7E-pETT1HP-1 transformed with the *H. polymorpha* ETT1 gene.

Not *S. cerevisiae* but *P. stipitis* ETT1 gene complement the ett1 mutation in *H. polymorpha*. To study the functional complementation of ett1 mutation of *H. polymorpha* two heterologous homologues were chosen: the *S. cerevisiae* MPE1 gene and the gene from *P. stipitis* (another xylose fermenting yeast species) herein designated PsETT1. The putative product of PsETT1 discovered to have about 37% amino acid identity with the HpEtt1 protein. The effect of expressing these heterologous genes was compared with the expression of the *H. polymorpha* HpETT1 gene a as a control. For this purpose the 7E mutant was transformed with plasmids p70+MPE1Sc, p70+ETT1Pst and pGLG61+ ETT1Hp (FIGS. 1.1-1.2). There it was shown that *S. cerevisiae* MPE1 gene did not restore the growth on the medium supplemented with 7% ethanol (FIG. 5). On the other hand, expression of the *P. stipitis* PsETT1 gene in the 7E mutant resulted in partial restoration of ethanol tolerance. The corresponding transformant 7E-GAPDHETT1Pst could grow on the medium with 7% ethanol although the growth was poor compared to those of the 3Leu+ and 7E-pETT1Hp-1 strains (FIG. 5). These data demonstrate that the genes of *H. polyporpha* and *P. stipitis* that are homologues of the MPE1 gene of *S. cerevisiae* are involved in ethanol tolerance. Accordingly the *H. polymorpha* and *P. stipitis* genes are hereby given the suffix designation "ETT1" for ethanol tolerance to distinguish them from MPE1 of *S. cerevisiae*. Another distinction is that expression of the *S. cerevisiae* MPE1 gene in *S. cerevisiae* is essential because a *S. cerevisiae* mutant in that gene is not viable, whereas in contrast, the *H. polymorpha* ett1 7E mutant isolated in herein is viable, although highly sensitive to exogenous ethanol.

Although the HpETT1 gene appears to be not essential for growth for *H. polymorpha*, the presence of RNA-binding zinc, knuckle domain in the HpETT1 gene suggest a possible involvement in RNA maturation, which may be one of the processes negatively affected by ethanol exposure in this and other organisms.

Figure 6:
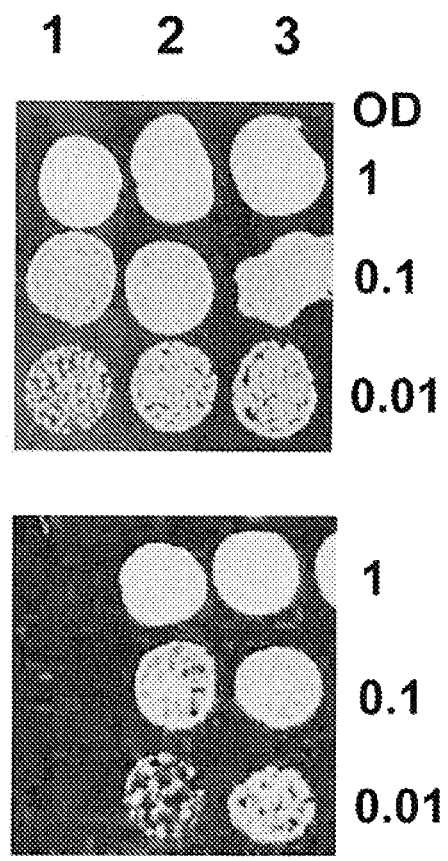
FIG. 6 depicts a solid media density assay showing enhanced ethanol tolerance in the strain 3Leu+pETT1-10 overexpressing the HpETT1 gene. The 3Leu+pETT1-10 strain was obtained by transformation of 3Leu+ strain with the multicopy integration vector pGLG61+ETT1HP. The upper panel shows growth on YPS media alone and the lower panel shows growth on the same plus 7% ethanol The strains are: (1) the 7E mutant; (2) the 3Leu+ control parent strain; and (3) the 3Leu+pETT1-10 strain, which is the control parent transformed with multiple copies of the *H. polymorpha* pETT1 gene.

Construction of *H. polymorpha* strain overexpressing native HpETT1 gene. The *H. polymorpha* 3Leu+ strain (Ishchuk et al., 2008) was transformed with plasmid vector pGLG61+ETT1Hp (FIG. 1f) for overexpressing the HpETT1 gene in *H. polymorpha*. Being a pGLG61 (Sohn et al., 1999) derivative the corresponding plasmid vector contains the telomeric sequence and the bacterial aminoglycoside 3-phosphotransferase (APH, genetecin resistance) gene. This vector promotes multicopy integration of plasmid tandem repeats into the genome (Sohn et al., 1999). The collection of geneticin resistant transformants was screened for improved ethanol resistance. The ethanol resistance varied among the transformants. This could be explained by different copy number of the plasmid integrated into the genome. The transformant 3Leu+pETT1-10 proved to be approximately 10-fold more tolerant to exogenous ethanol compared to the recipient parent strain 3Leu+ (FIG. 6). The copy number of the HpETT1 gene in the transformant was estimated by Southern blotting (FIG. 3B). Comparing the intensity of the signal to the 3Leu+ strain which contains only one copy of the HpETT1 gene, it was determined that the 3Leu+pETT1-10 transformant carries approximately 6-7 copies in its genome.

Figure 7:
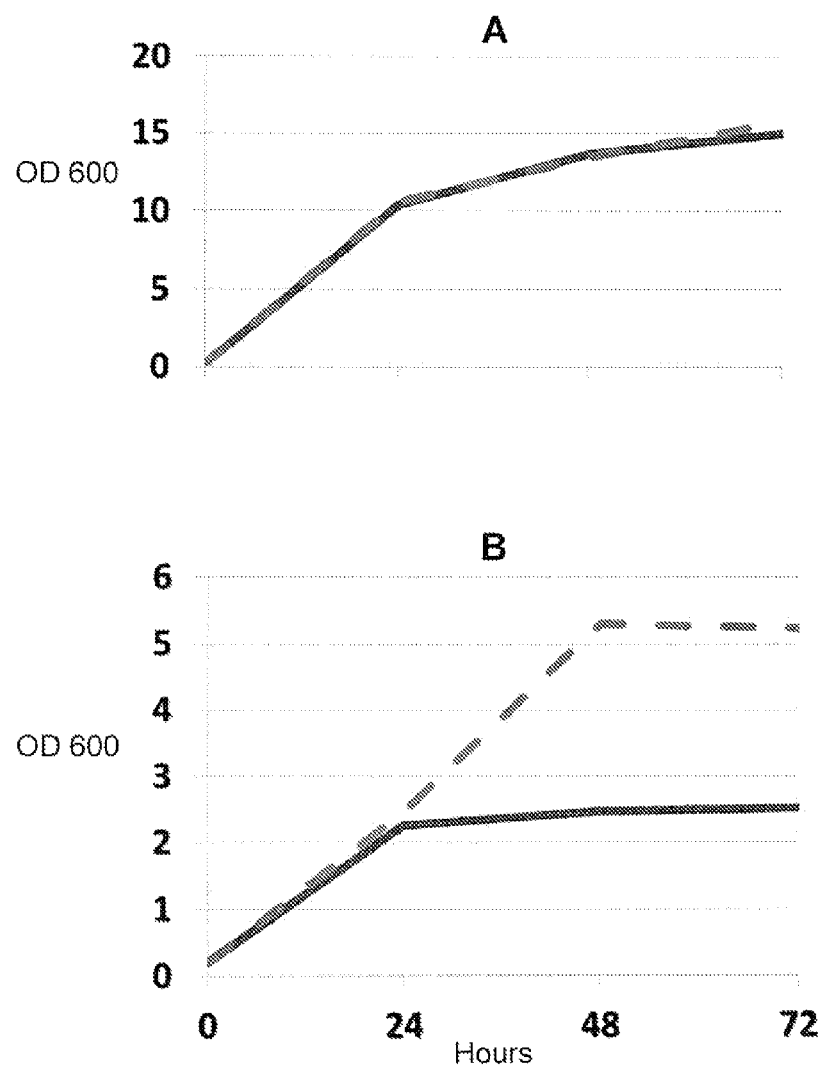
FIG. 7 are graphs showing enhanced ethanol tolerance in growth characteristics of strain 3leu+pETT1-10 overexpressing the HpETT1 gene in *H. polymorpha* (dotted lines) in comparison to the control strain 3Leu+ (solid lines) when grown in YPD medium lacking ethanol (A) and in the same medium containing 6% ethanol (B).
Figure 8:
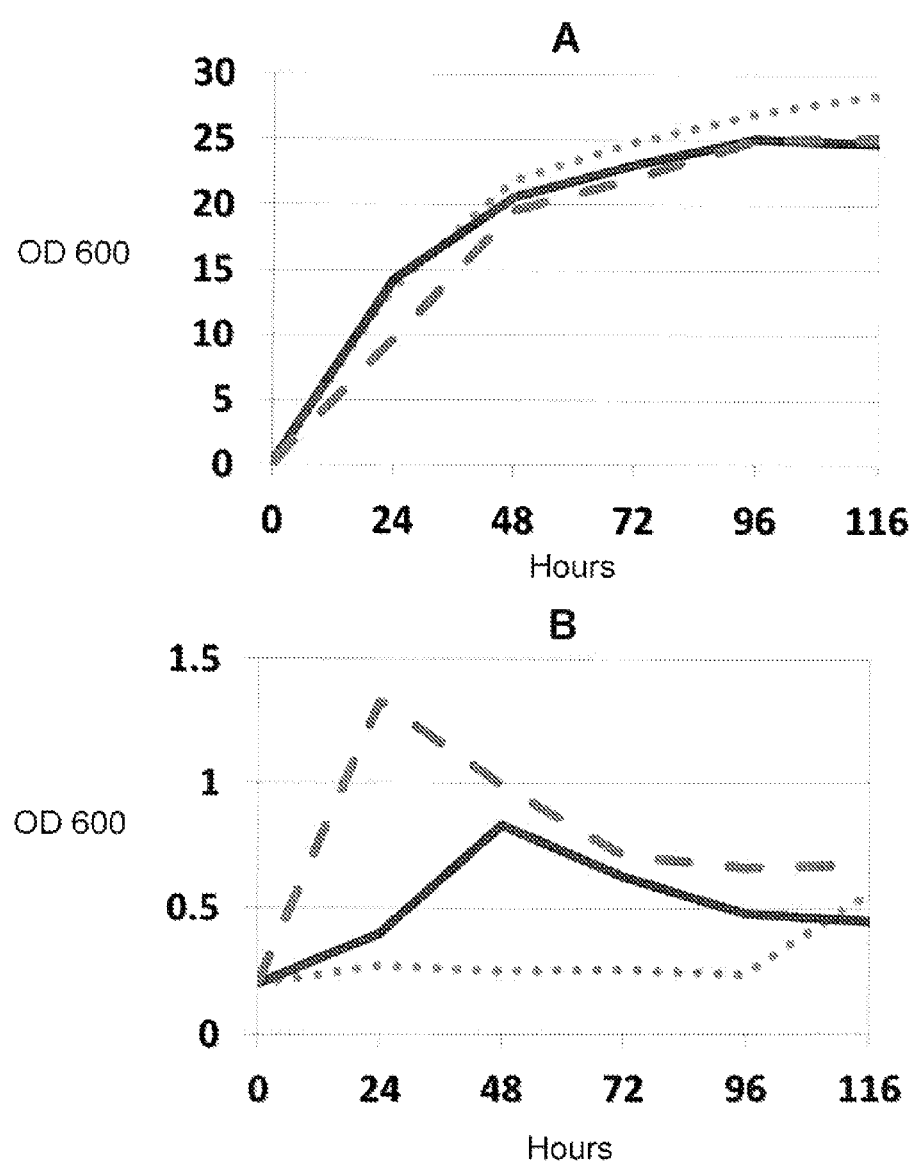
FIG. 8 are graphs showing ethanol sensitivity of the 7E mutant (dotted lines) and enhanced ethanol tolerance in growth characteristics of strain 3Leu+pETT1-10 (dashed lines) overexpressing the HpETT1 gene in *H. polymorpha* in comparison to the control parent strain 3leu+ (solid lines) on YPS medium alone (A) or the same containing 7% ethanol (B).

The *H. polymorpha* HpETT1 multicopy integrant has improved growth on the medium with ethanol. Tolerance of *H. polymorpha* strains to ethanol was measured as the viability in the presence of ethanol in liquid YPD/YPS media. In the media without ethanol there was no difference between strains growth (FIG. 7A, FIG. 8A). The 3Leu+ pETT1-10 transformant had improved growth on both 6% and 7% ethanol media (FIG. 7B, FIG. 8B). At cultivation time of 48 and 72 hours the growth density of the multicopy HpETT1 integrant was 2-fold higher than the 3Leu+ strain in the 6% ethanol medial. Under conditions of cultivation in 7% ethanol medium (FIG. 8B) a difference in growth rate and density was observed within the first day of incubation and was 3.4 times higher for the 3Leu+pETT1-10 transformant compared to the parent recipient strain 3Leu+. However, during prolonged cultivation (48, 72 and 96 hours) all strains exhibited a decline in growth, although the growth kinetics of the HpETT1 multicopy integrant was observably better throughout the cultivation period. As noted before, the 7E mutant which is hypersensitive to ethanol, showed impaired growth on the 7% ethanol medium.

Figure 9:
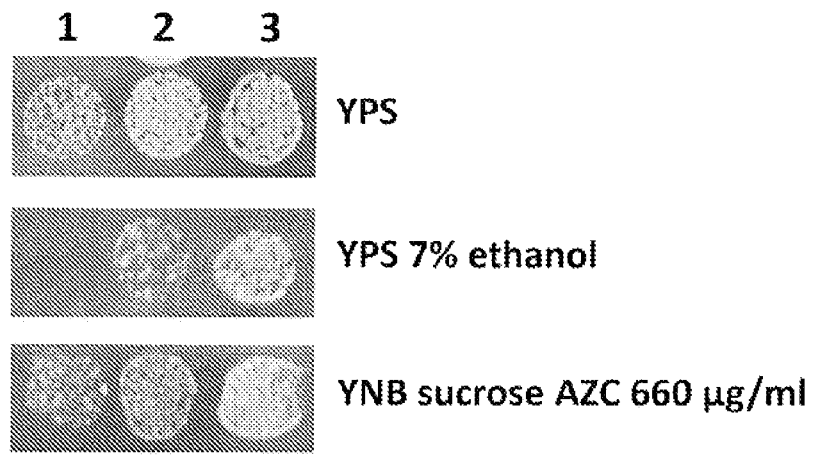
FIG. 9 shows increased stress tolerance in the 3Leu+ ETT1-10 (3) strain overexpressing the HpETT1 gene by growth on solid media with and without ethanol or the stress inducing agent AZC in comparison to the parent control strain 3leu+ (2) and the mutant strain 7E strain (1).
Figure 10:
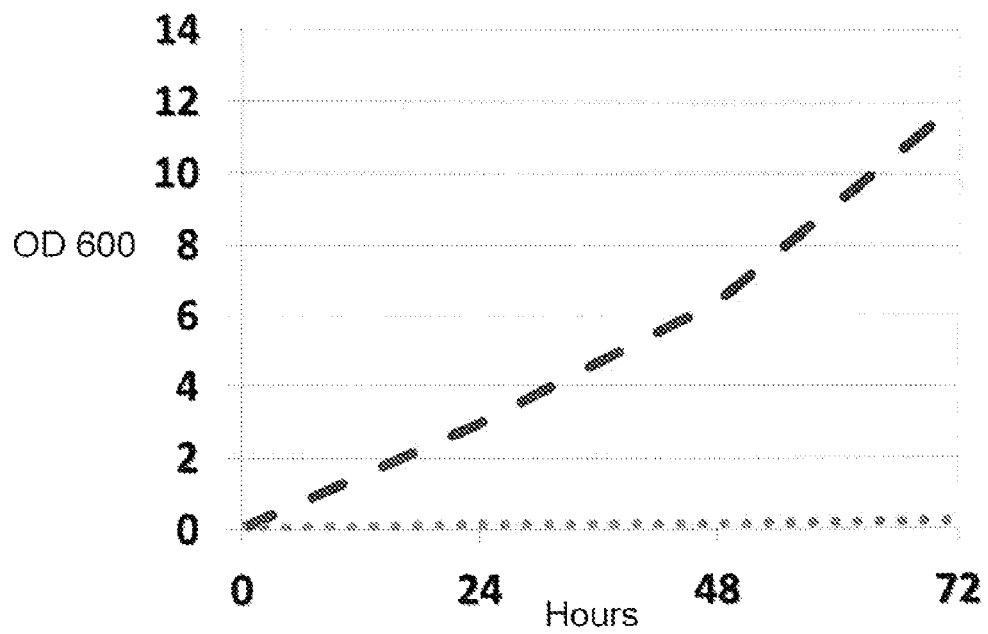
FIG. 10 is a graph depicting temperature sensitivity of the *H. polymorpha* 7E mutant (dashed line) in comparison with its parental strain 3leu+ (solid line).
Figure 11:
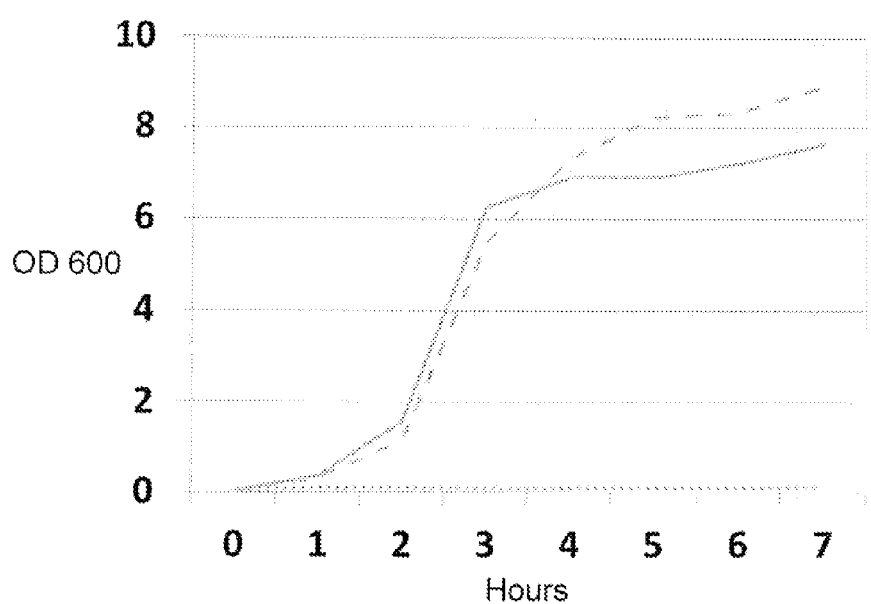
FIG. 11 is a graph showing improved growth characteristics of the strain 3Leu+pETT1-10 overexpressing the HpETT1 gene (dashed line) when grown in YNB media using 2% xylose as the carbon source at 50° C. in comparison to the 7E mutant (dotted line) and the parental strain 3leu+ (solid line).
Figure 13:
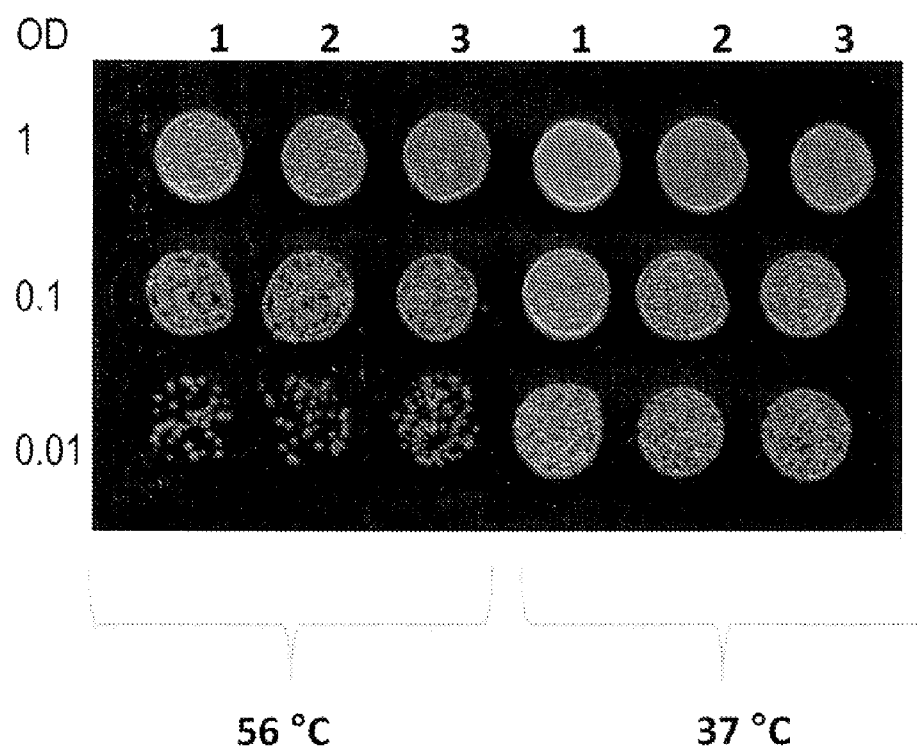
FIG. 13 depicts a solid media density assay showing increased heat shock tolerance of the 3Leu+pETT1-10 strain of *H. polymorpha* overexpressing the HpETT1 gene (3) in comparison to the parental control 3leu+ (2) and the strain MPE1Sc, which is 3Leu+ transformed with a vector to overexpress the *S. cerevisiae* MPE1 protein, when grown at 37° C. or heat shocked at 56° C. for 15 min prior to plating.

The *H. polymorpha* ETT1 multi-copy integrant is resistant to other kinds of stress. The 3Leu+pETT1-10 transformant is also more resistant to the proline analogue 2-azetidine carboxylic acid, AZC (FIG. 9) than the parent recipient strain. AZC is incorporated into proteins competitively with proline and results in protein misfolding (Lane et al., 1971; Zagari et al., 1990), and this compound is known to induce the expression of heat-shock proteins. Thus the effect of AZC treatment is a stress response that resembles that of heat-shock (Trotter et al., 2002). This likely explains why the 7E mutant does not grow well at 50° C. compared to the 3Leu+ parent strain (FIG. 10, FIG. 11). Further evidence that the product of the HpETT1 is related to a heat shock response is that the 3Leu+pETT1-10 transformant that overexpresses HpETT1 displays slightly improved growth at 50° C. comparing to the 3Leu+ strain (FIG. 11) and is more tolerant to heat-shock (FIG. 13).

Figure 12:
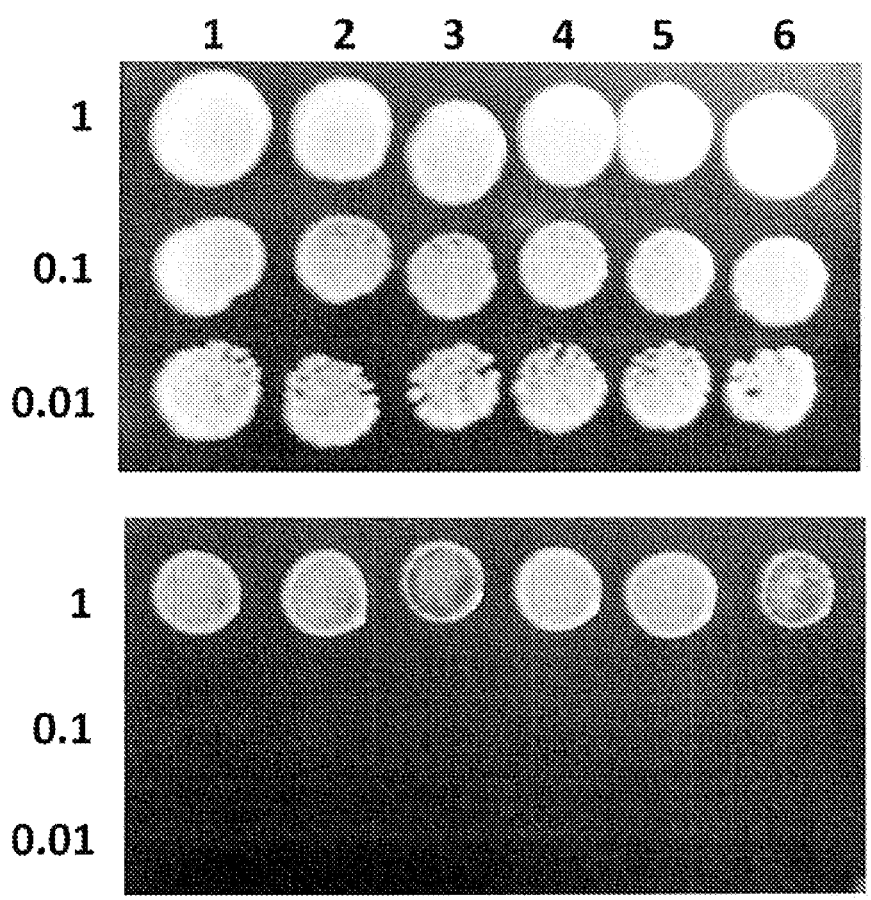
FIG. 12 depicts a solid media density assay showing increased ethanol tolerance in at least two *S. cerevisiae* strains (4 and 5) expressing the HpETT1 gene from *H. polymorpha*. Strain 1 is the control strain carrying only the *S. cerevisiae* plasmid vector Yep352, and strains 2-6 were separate isolates of transformants with that vector but carrying the *H. polymorpha* HpETT1 gene under control of a *S. cerevisiae* promoter. The upper panel is the control growth media (YNB plus sucrose, leu, lys and his) the lower panel is the same further containing 6% ethanol.

Overexpression of the *H. polymorpha* HpETT1 gene in *S. cerevisiae* increases ethanol tolerance. The *H. polymorpha* HpETT1 gene was cloned into a yeast expression vector under control of the *S. cerevisiae* PGK1 promoter. Two transformants showed slightly increased growth on ethanol media (FIG. 12). As with the case of expression in *H. polymorpha* increased ethanol tolerance will likely be observed when *S. cerevisiae* is transformed with the expression vector in high-copy number.

Figure 14:
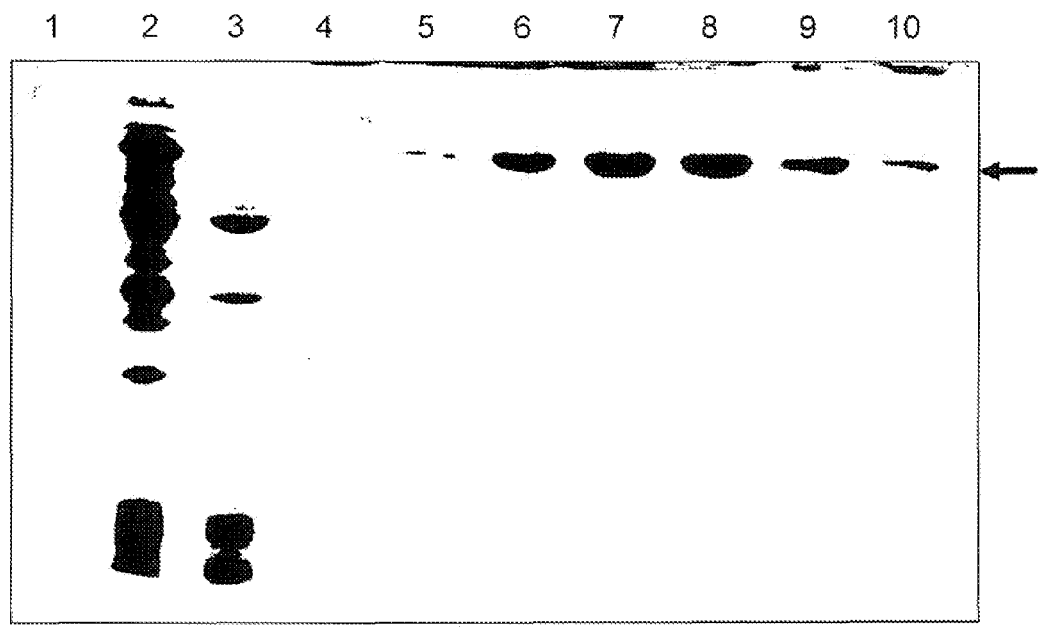
FIG. 14 shows a 12% SDS PAGE result demonstrating isolation of the HpEtt1 protein (arrow) after overexpression in *E. coli* using a his-tagged expression vector. Lane assignments: 1, protein ladder; 2, total soluble proteins before column; 3 soluble protein flow through; 4-9 fractions subsequently eluted from column.

Purification of *H. polymorpha* HpEtt1 protein. The *H. polymorpha* HpEtt1 protein was overexpressed in bacteria as his tagged fusion protein, then isolated and partially purified as shown in the SDS polyacrylamide gel depicted in FIG. 14.

Discussion. The *S. cerevisiae* Mpe1 protein as previously characterized as an essential evolutionary conserved protein participating in cleavage and polyadenylation of mRNA (Vo et al., 2001). The present disclosure demonstrates that an orthologue present in *H. polymorpha* that shares 39% sequence identity with the *S. cerevisiae* Mpe1 protein, which is herein designated HpEtt1 is involved in ethanol resistance and high temperature resistance in *H. polymorpha* and also confers a detectable increase in ethanol resistance when expressed in *S. cerevisiae*. Unlike its *S. cerevisiae* orthologue, the HpETT1 gene is not necessary for cell viability. The ability to functionally complement the *H. polymorpha* 7E mutant was used as a method to isolate another Ett1 like protein PsEtt1 from another xylose fermenting yeast. *P. stipitis*. The PsEtt1 protein shares about 37% amino acid identity with the HpEtt1. Despite having similar sequence identity at 39% to the *S. cerevisiae* homologue MPE1, expression of the *S. cerevisiae* protein in the *H. polymorpha* 7E mutant, which lacks a functional HpETT1 gene did not restore the growth on 7% ethanol. In spite of being evolutionary conserved, Ett1p of *H. polymorpha* as well as other xylose fermenting yeast species *P. stipitis* participate in ethanol resistance. It is noted that the sequence of the *H. polmorpha* HpETT1 contains several motifs (FIG. 4) recognized in the *S. cerevisiae* gene to be involved in mRNA maturation (i.e., an RNA-binding zinc knuckle domain) (Vo et al., 2001). The question about involving the *H. polymorpha* HpETT1 gene in mRNA maturation remains unclarified pending experimental evaluation.

The results described herein show that *H. polymorpha* ethanol tolerance could be substantially improved by introducing multiple copies of native ETT1 gene into the genome. The strain constructed in the present disclosure is a recombinant strain carrying 6-7 copies of ETT1 gene and has 10-fold higher resistance towards exogenous ethanol and improved growth kinetics in the ethanol media. Moreover, the corresponding multicopy integrant (3Leu+pETT1-10) proved to be more resistant to the protein misfolding reagent, AZC. The 7E mutant is unable to grow at 50° C., which is upper temperature limit to *H. polymorpha* (Guerra et al., 2005). Ethanol and temperature stresses cause some similar effects, particularly block of mature mRNA export from the nucleus and subsequently the accumulation of bulk poly $(A)^+$mRNA in this cell compartment (Tani et al., 1995; Saavedra et al, 1996; Krebber et al., 1999). The defects in processes of mRNA maturation also cause the accumulation of bulk poly $(A)^+$mRNA in the nucleus (Brodsky and Silver, 2000; Jensen et al., 2001). So it may be supposed that *H. polymorpha* Ett1Hp being a RNA-binding protein could influence the mRNA maturation under ethanol stress and high temperature but not under optimal growth conditions.

REFERENCES

Brachmann, C. B., A. Davies, G. J. Cost, E. Caputo, J. Li, P. Hieter, and J. D. Boeke. 1998. Designer strains derived from *Saccharomyces cerevisiae* S288C: useful set of strains and plasmids for PCR-mediated gene disruption and other applications Yeast 14: 115-132.

Brodsky, A. S. and Silver, P. A. (2000). Pre-mRNA processing factors are required for nuclear export. RNA 6: 1737-1749.

Faber, K. N., P. Haima, W. Harder, M. Veenhuis, and G. Ab, 1994. Highly-efficient electrotransformation of the yeast *Hansenula polymorpha*. Curr Genet 25(4): 305-310.

Gellissen, G. 2000. Heterologous protein production in methylotrophic yeasts. Appl. Microbiol. Biotechnol. 54: 741-750.

Gellissen, G. (ed.), 2002. *Hansenula polymorpha*—Biology and Applications. Wiley-VCH, Weinheim.

Gleeson, M. A. G, and P. E. Sudbery. 1988. Genetic analysis in the methylotrophic yeast *Hansenula polymorpha*. Yeast 4: 293-303.

Guerra, E., P. P. Chye, E. Berardi and P. W. Piper, 2005. Hypoxia abolishes transience of the heat-shock response in the methylotrophic yeast *Hansenula polymorpha*. Microbiology 151: 805-811.

Ishchuk, O. P., A. Y. Voronovsky, O. V. Stasyk, G. Z. Gayda, M. V. Gonchar, C. A. Abbas, and A. A. Sibirny. 2008. Overexpression of pyruvate decarboxylase in the yeast *Hansenula polymorpha* results in increased ethanol yield in high-temperature fermentation of xylose. FEMS Yeast Res 7: 1167-1174.

Jensen, T. H., K. Patricia, T. McCarthy and M. Rosbash. 2001. A block to mRNA nuclear export in *S. cerevisiae* leads to hyperadenylation of transcripts that accumulate at the site of transcription. Mol Cell 7: 887-898.

Krebber, H., T. Taura, M. S. Lee and P. A. Silver. 1999. Uncoupling of hnRNP Npl3p from mRNAs during the stress-induced block in mRNA export. Genes Dev 13: 1994-2004.

Lahtchev, K. L., V. D. Semenova, I. I. Tolstorukov, I. van der Klei, and M. Veenhuis. 2002. Isolation and properties of genetically defined strains of the methylotrophic yeast *Hansenula polymorpha* CBS4732, Arch. Microbiol. 177 150-158.

Lane, J. M., P. Dehm, and D. J. Prockop. 1971. Effect of the proline analogue azetidine-2-carboxylic acid on collagen synthesis in vivo. I. Arrest of collagen accumulation in growing chick embryos. Biochim Biophys Acta 236(3): 517-527.

Ryabova, O. B., O. M. Chmil, and A. A. Sibirny, 2003. Xylose and cellobiose fermentation to ethanol by the thermotelerant methylotrophic yeast *Hansenula polymorpha*. FEMS Yeast Res. 4(2): 157-164.

Saavedra, C., K. S. Tung, D. C. Amberg, A. K. Hopper, and C. N. Cole, 1996. Regulation of mRNA export in response to stress in *Saccharomyces cerevisiae*. Genes Dev 10: 1608-1620.

Sambrook, J., E. F. Fritsh, and T. Maniatis. 1989, Molecular Cloning: A Laboratory Manual, 2nd edition., Cold Spring Harbor, N.Y.: Cold Spring Harbor Laboratory.

Siverio, J. M. 2002. Biochemistry and genetics of nitrate assimilation. In—Gellissen (ed.), *Hansenula polymorpha*—Biology and Applications. Wiley-VCH, Weinheim.

Sohn, J. H, E. S. Choi, H. A. Kang, J. S. Rhee, M. O. Agaphonov, M. D. Ter-Avanesyan, and S. K. Rhee. 1999. A dominant selection system designed for copynumber-controlled gene integration in *Hansenula polymorpha* DL-1. Appl. Microbiol. Biotechnol. 51: 800-807.

Suckow, M., and G. Gellissen. 2002. The expression platform based on *H. polymorpha* strain R811 and its derivatives—history, status and perspectives. In G. Gellissen (ed.), *Hansenula polymorpha*—Biology and Applications. Wiley-VCH, Weinheim.

Tani, T., R. J. Derby, Y. Hiraoka, and D. L. Spector. 1995. Nuclear accumulation of poly (A)+ RNA in heat-shocked yeast cells: implication of nucleolar involvement in mRNA transport, Mol. Biol. Cell 6: 1515-1534.

Trotter, E. W., C. M. Kao, L. Berenfeld, D. Botstein, G. A. Petsko, and J. V. Gray. 2002, Misfolded proteins are competent to mediate a subset of the responses to heat shock in *Saccharomyces cerevisiae*. J Biol Chem 277(47): 44817-44825.

Ubiyvovk, V. M, O. V. Blazhenko, D. Gigot, M. Penninckx, and A. A. Sibirny. 2006. Role of gamma-glutamyl-transpeptidase in detoxification of xenobiotics in the yeasts *Hansenula polymorpha* and *Saccharomyces cerevisiae*. Cell Biol Int 30: 665-671.

Van der Klei, I. L, and M. Veenhuis. 2002. *Hansenula polymorpha*: a versatile model organism in peroxisome research. In G. Gellissen (ed.), *Hansenula polymorpha*—Biology and Applications. Wiley-VCH, Weinheim.

Vo, L. T., M. Minet, J. M. Schmitter, F. Lacroute, and F. Wyers, 2001. Mpe1, a zinc knuckle protein, is an essential component of yeast cleavage and polyadenylation factor required for the cleavage and polyadenylation of mRNA. Mol. Cell Biol. 21(24): 8346-8356.

Voronovsky, A., C. A. Abbas, L. R. Fayura, B. V. Kshanovska, K. V. Dmytruk, K. A. Sybirna and A. A. Sibirny. 2002. Development of a transformation system for the flavinogenic yeast *Candida famata*. FEMS Yeast Res. 2: 381-388.

Yang, V. W., J. A. Marks, B. Davis, and T. Jeffries. 1994. High-efficiency transformation of *Pichia stipitis* based on its URA3 gene and a homologous autonomous replication sequence, ARS2, Appl. Environ. Microbiol. 60: 4245-4254.

Zagari, A., G. Némethy, and H. A. Scheraga. 1990. The effect of the L-azetidine-2-carboxylic acid residue on protein conformation. I. Conformations of the residue and of dipeptides. Biopolymers 30(9-10): 951-959.

The invention claimed is:

1. A method of identifying a gene that confers enhanced ethanol tolerance in a yeast comprising, transforming a parent *H. polymorpha* strain that has a mutation in the ETT1 gene encoding a protein according to SEQ. ID NO: 2 where the mutation results in sensitivity to growth on medium containing ethanol in comparison to a parent strain of *H. polymorpha* that lacks such a mutation with a candidate nucleic acid operably linked to a promoter that expresses a protein encoded by the candidate nucleic acid; selecting a transformed daughter strain of *H. polymorpha* that exhibits enhanced growth on a media comprising ethanol relative to the mutant parental strain; and determining a sequence for the candidate nucleic acid expressed in the selected transformed daughter strain, thereby identifying a gene that confers ethanol tolerance.

2. The method of claim 1 wherein the gene that confers ethanol tolerance encodes a protein having at least 39% sequence identity to the *S. cerevisiae* MPE1 protein according to SEQ. ID NO: 6.

3. The method of claim 1 wherein the gene that confers ethanol tolerance encodes a protein having at least 37% sequence identity to the *H. polymorpha* ETT1 protein according to SEQ. ID NO: 2.

4. The method of claim 1 wherein the gene that confers ethanol tolerance encodes a protein having at least 37% sequence identity to the *P. stipitis* ETT1 protein according to SEQ. ID NO: 4.

5. The method of claim 1 wherein the daughter strain is transformed with a vector that introduces multiple copies of the gene that confers ethanol tolerance into a chromosome of the daughter strain.

* * * * *

SEQUENCE LISTING

```
<160> NUMBER OF SEQ ID NOS: 14

<210> SEQ ID NO 1
<211> LENGTH: 1122
<212> TYPE: DNA
<213> ORGANISM: Hansenula polymorpha

<400> SEQUENCE: 1
atggctgtca tatactataa gttcagatcg caacgcgatg acttgatttc gaccatcaag      60
tttgatggta ctgggcttac ggtattcgaa ctcaaacgag aaattattta tgccaataag     120
ctgattaatt ccacggacac agatatttta ttatatcatg ttgaagatcc agataaggag     180
tacgacgatg ataatgaagt catacaacga gcatcaacag tgctagtaag aagaacttca     240
ggtggcaaga aaggaagagg aaacgttttg cgatatatgg caggaaagcc aaggattgca     300
aaatttcaag ctccgattcc agtctcaacg acagattcag caccggtcat acctactaat     360
gaagaggaga gaattcgtca gatgttcaat cagcaggacg accagtggaa tcaacaacag     420
gctctcatgg ccactgcaca aagagtggaa agtaatagac aaaatttgaa acttgatgaa     480
aacattcctg aatattacat ttgctataaa tgcggcgaga aagggaaaca tcatattaga     540
aactgtccaa agaataatga tcccaattgg gatggcatca ggatcaaaaa aacgactgga     600
ataccaaaat cgtatttacg cactgttgat aatccgactg acatcgtcaa cgaacctaat     660
cagaacttca tggtgaatga gagggaaaa tacgtggtgg cagttgctga taaaaaagcg      720
tggcaaagat atcagaccat tcagcaatct aagcaagagg aagacgattt cccgattgaa     780
gatcctgaac taagggatcc tcattcaggt aagctttgga aaactcctgt gagaactaaa     840
tgttgcaaac aactgtattc aagaccttac attgaagatc tacttttgga gtcagatttc     900
aagtgtccga attgtggtca agaggacatt tatcttgatt ctcttgaagt cgacgaggca     960
ttacagcgaa aggtagattt gtttgtggaa caacataaga gaaaaaatga aagggaagaa    1020
gagccgaaca agcggcaaca cttagctaca atggtaccta ctatgatgcc atttatgccg    1080
tttccagccc cattgcctct accgaccaat aatcaaaagt ga                        1122

<210> SEQ ID NO 2
<211> LENGTH: 373
<212> TYPE: PRT
<213> ORGANISM: Hansenula polymorpha

<400> SEQUENCE: 2

Met Ala Val Ile Tyr Tyr Lys Phe Arg Ser Gln Arg Asp Asp Leu Ile
1               5                   10                  15

Ser Thr Ile Lys Phe Asp Gly Thr Gly Leu Thr Val Phe Glu Leu Lys
            20                  25                  30

Arg Glu Ile Ile Tyr Ala Asn Lys Leu Ile Asn Ser Thr Asp Thr Asp
        35                  40                  45

Ile Leu Leu Tyr His Val Glu Asp Pro Asp Lys Glu Tyr Asp Asp Asp
    50                  55                  60

Asn Glu Val Ile Gln Arg Ala Ser Thr Val Leu Val Arg Arg Thr Ser
```

```
                65                  70                  75                  80
            Gly Gly Lys Lys Gly Arg Gly Asn Val Leu Arg Tyr Met Ala Gly Lys
                            85                  90                  95
            Pro Arg Ile Ala Lys Phe Gln Ala Pro Ile Pro Val Ser Thr Thr Asp
                        100                 105                 110
            Ser Ala Pro Val Ile Pro Thr Asn Glu Glu Arg Ile Arg Gln Met
                    115                 120                 125
            Phe Asn Gln Gln Asp Asp Gln Trp Asn Gln Gln Ala Leu Met Ala
                130                 135                 140
            Thr Ala Gln Arg Val Glu Ser Asn Arg Gln Asn Leu Lys Leu Asp Glu
            145                 150                 155                 160
            Asn Ile Pro Glu Tyr Tyr Ile Cys Tyr Lys Cys Gly Glu Lys Gly Lys
                            165                 170                 175
            His His Ile Arg Asn Cys Pro Lys Asn Asn Asp Pro Asn Trp Asp Gly
                        180                 185                 190
            Ile Arg Ile Lys Lys Thr Thr Gly Ile Pro Lys Ser Tyr Leu Arg Thr
                    195                 200                 205
            Val Asp Asn Pro Thr Asp Ile Val Asn Glu Pro Asn Gln Asn Phe Met
            210                 215                 220
            Val Asn Glu Glu Gly Lys Tyr Val Val Ala Val Ala Asp Lys Lys Ala
            225                 230                 235                 240
            Trp Gln Arg Tyr Gln Thr Ile Gln Gln Ser Lys Gln Glu Glu Asp Asp
                            245                 250                 255
            Phe Pro Ile Glu Asp Pro Glu Leu Arg Asp Pro His Ser Gly Lys Leu
                        260                 265                 270
            Trp Lys Thr Pro Val Arg Thr Lys Cys Cys Lys Gln Leu Tyr Ser Arg
                    275                 280                 285
            Pro Tyr Ile Glu Asp Leu Leu Leu Glu Ser Asp Phe Lys Cys Pro Asn
                290                 295                 300
            Cys Gly Gln Glu Asp Ile Tyr Leu Asp Ser Leu Glu Val Asp Glu Ala
            305                 310                 315                 320
            Leu Gln Arg Lys Val Asp Leu Phe Val Glu Gln His Lys Arg Lys Asn
                            325                 330                 335
            Glu Arg Glu Glu Glu Pro Asn Lys Arg Gln His Leu Ala Thr Met Val
                        340                 345                 350
            Pro Thr Met Met Pro Phe Met Pro Phe Pro Ala Pro Leu Pro Leu Pro
                    355                 360                 365
            Thr Asn Asn Gln Lys
                370

<210> SEQ ID NO 3
<211> LENGTH: 1425
<212> TYPE: DNA
<213> ORGANISM: Pichia stipitis

<400> SEQUENCE: 3
atgtcgtcag tcgtctacta taagttttt caccagaaga accggtcagt gatccacttt     60
gacggtacag ctatatccgt cttcgatctc aagcgagaga ttatccagca gaaccagcta    120
ggactgggtc ttgacttcaa tttacgttta tatcattcag aactgcccga cacagagtat    180
gagttagacc aggatgtcat accgaggtcg tcctacgtct tggcgaaaag gtctcctgct    240
atatttagga acagatttag taccaatgct tccagatatg ttacaggaaa gccacggatc    300
aacagaaaag ccatcaacac cgctggaata acgactggtg tcacaggacc aactctcggc    360
```

-continued

```
caaagaccag tggacgaaaa catttcggaa gaagatcgaa tcaagttgat gtttgagaac      420
caggagaatg cctgggccca gactcaggac gagttggcca ctcacaaaat gatacactac      480
aagcctggag ccgctggagc taaggaagac ttaccgccac caggttatat ttgctataga      540
tgtgggaaga aagaccactg gatcaagaac tgtcctacga caacgaccc  caatttcgag      600 ggaaagaagg tcttgcgtac gaccggtatt ccaaagtcgt atttgaagac aatttctaag      660
gaggagtttg acaagaaaat ggagaccgat gcttttgaaa ctaacgaaaa tggagacatt      720
attgatagcg aaggcaatgc catttttagtg acagaagacg gagactatgc catagccatg      780
gctgacagca agacctggct cacataccag gaaaagcaac agaatgctgc cttgaaggca      840
cagcaggact ttgaaaagaa gatagtggct tgcatagaaa acgataatcg agcagagttc      900
ttggatcctc tagcttccac taagaagttg ctcaagtcgc ccatagtgat gacaccatgt      960
tgcaccgaaa agtccaaatt gaacaaaatg accaatttca gctataacaa aagcgcattg     1020
gagcaggtat taattgagaa tgacttccat tgccccaact gtaacaccga agatatcttc     1080
atcgattcct tgattcccaa tgaagagtta gagtcgcagt tgaaacagta catcgaagag     1140
aaacacacag aactaggcat agagattcca ggctcagaaa gcacattaaa gagatcagcg     1200
gacgatgcag atgaaatagg cccagatgct aaaagacaac gtccagaaat ggccacccca     1260
tttggtcaaa tgatgcctgg aatgcccatg ccacctccag gagtcatgcc acctccagga     1320
gtcatgcctg ctcctttttgc tatccctcca ggtatgccca tccctcctcc cggtatgcca     1380
atgttcatgc ctttcagcaa tgtcaataac cagaagaaga attag                     1425
```

<210> SEQ ID NO 4
<211> LENGTH: 498
<212> TYPE: PRT
<213> ORGANISM: Pichia stipitis

<400> SEQUENCE: 4

```
Met Ser Ser Val Val Tyr Tyr Lys Phe Leu His Gln Lys Asn Lys Ser
1               5                   10                  15

Val Ile His Phe Asp Gly Thr Ser Ile Ser Val Phe Asp Leu Lys Lys
            20                  25                  30

Glu Ile Ile Ile Gln Asn Gln Leu Gly Ser Gly Gln Asp Phe Asn Leu
        35                  40                  45

Arg Leu Tyr His Ser Glu Gln Pro Asp Gln Glu Tyr Glu Leu Asp Gln
    50                  55                  60

Asp Val Ile Pro Arg Ser Ser Tyr Val Leu Ala Lys Arg Ser Pro Ala
65                  70                  75                  80

Phe Val Lys Ser Gly Lys Tyr Asn Asn Ala Ser Arg Tyr Ile Thr Gly
                85                  90                  95

Lys Pro Arg Ile Asn Arg Lys Ala Ile Thr Ser Thr Val Gly His Asn
            100                 105                 110

Ser Asn Ser Asn Pro Leu Val Ser Ala Gln Leu Gln Gln Gln Gln Gln
        115                 120                 125

Gln Gln Leu Asp Glu Asn Ala Thr Glu Glu Asp Arg Ile Lys Leu Met
    130                 135                 140

Phe Gln Asn Gln Ser Asn Ala Trp Glu Gln Thr Gln Glu Asp Leu Ala
145                 150                 155                 160

His His Lys Met Val Phe Asn Lys Pro Thr Ala Ser Ser Thr Ala Asn
                165                 170                 175

Lys Gln Asp Asp His Pro Pro Pro Gly Tyr Ile Cys Tyr Arg Cys Gly
            180                 185                 190
```

```
Lys Lys Asp His Trp Ile Lys Asn Cys Pro Thr Asn Asp Pro Asn
            195                 200                 205
Phe Glu Gly Lys Lys Ile Met Arg Thr Thr Gly Ile Pro Lys Ser Tyr
    210                 215                 220
Leu Lys Thr Ile Ser Arg Glu Glu Val Glu Ser Lys Ala Asn Thr Leu
225                 230                 235                 240
Thr Thr Asn Asp Asn Gly Asp Val Val Asp Ser Glu Gly Asn Val Ile
                245                 250                 255
Leu Ile Thr Asp Asp Gly Asp Tyr Ala Ile Ala Met Ala Asp Ser Lys
            260                 265                 270
Thr Trp Gln Asn Tyr Gln Glu Lys Leu Gln Asn Ala Ala Leu Lys Ser
        275                 280                 285
Lys Arg Glu Tyr Glu Ser Lys Leu Val Ala Glu Ile Glu Lys Asp Asn
    290                 295                 300
Lys Trp Glu Phe Leu Asp Pro Leu Ala Asn Thr Lys Ala Val Leu Thr
305                 310                 315                 320
Ser Pro Ile Val Met Thr Pro Cys Cys Thr Asp Ser Ser Lys Leu Gln
                325                 330                 335
Asn Leu Lys Asn Phe Asn Tyr Asn Gln Pro Glu Leu Glu Arg Val Leu
            340                 345                 350
Ile Asp Asn Asp Phe His Cys Pro Asn Cys Gly Lys Ala Asp Val Phe
        355                 360                 365
Leu Asp Ser Val Ile Pro Asn Lys Asp Leu Glu Glu Lys Leu Lys Glu
    370                 375                 380
Tyr Val Ser Ser Lys Glu Lys Glu Leu Asn Ile Lys Asp Pro Ser Lys
385                 390                 395                 400
Arg Thr Ala Ala Glu Met Thr Ala Asp Asp Asn Asn Asp Pro His His
                405                 410                 415
Ser Gly Glu Pro Asp Ala Lys Lys Gln Lys Ile Val Pro Asn Thr Val
            420                 425                 430
Gln Pro Gly Met Phe Pro Val Gly Val Met Pro Pro Pro Pro Pro
        435                 440                 445
Met Pro Phe Ala Leu Pro Pro Gly Leu Gln Ile Pro Pro Pro Gly Phe
    450                 455                 460
Gly Met Val Pro Pro Pro Asn Phe Met Pro Pro Thr Gln Gly Gln Gln
465                 470                 475                 480
Phe Asn Asn Asn Asn Asn Asn Asn Ser Asn Asn Gln Phe Asn Gln
                485                 490                 495
Pro Lys

<210> SEQ ID NO 5
<211> LENGTH: 1326
<212> TYPE: DNA
<213> ORGANISM: Saccharomyces cerevisiae

<400> SEQUENCE: 5
atgagtagca cgatatttta ccgctttaag tctcaacgaa acacatcaag aattttattt      60
gatggtaccg gcctgacagt atttgatttg aaaagggaaa ttattcaaga gaacaaacta     120
ggtgacggca cagatttcca attaaaaatt tacaacccag atacagaaga ggaatacgac     180
gatgatgcct ttgttatacc tagatctact agtgtcatag taaaaagatc tccagcaatt     240
aaatcattct ccgtacacag tcgacttaaa gggaatgtgg agcagcagc tcttgggaac      300 gcaacaaggt atgttactgg taggccaaga gtgttgcaaa agagacaaca cactgctaca     360
```

-continued

```
accactgcta atgttagtgg tacaacggaa gaagaaagaa ttgctagtat gtttgccaca    420
caagaaaatc aatgggaaca aacgcaagaa gaaatgtctg cagccacacc tgttttttc     480 aagtcacaga cgaataagaa ttctgcacaa gaaaacgaag gcccaccgcc accaggttat    540
atgtgctatc gttgtggggg tagagaccac tggattaaaa attgtccaac taacagcgat    600
ccaaattttg aaggaaaaag aatcagaaga accacaggta ttccaaagaa gttttttaaaa  660 tccattgaaa tagatcccga gacaatgaca ccggaagaga tggctcagcg aaagattatg    720
attacggacg aaggcaagtt cgtggtacaa gttgaagaca acaatcatg ggaagactac      780 caaaggaaaa gagagaaccg tcaaattgat ggtgatgaaa ccatttggag aaaaggccat    840
ttcaaagatc ttcctgacga tttaaaatgt cccttgacag gtggtctttt gaggcagccg    900
gtaaagacaa gcaagtgctg taacatagat ttctcaaaag aggcgctgga aaatgcactg    960
gtagagagcg actttgtatg ccccaattgc gaaacccgcg atatccttct cgattcttta    1020
gtacccgacc aggacaagga aaaggaggtc gaaacgtttt tgaagaaaca agaggaacta    1080
cacggaagct ctaaagatgg caaccagcca gaaactaaga aaatgaagtt gatggatcca    1140
actggcaccg ctggcttgaa caacaatacc agccttccaa cttctgtaaa taacggcggt    1200
acgccagtgc caccagtacc gttacctttc ggtatacctc cttttcccat gtttccaatg    1260
cccttcatgc ctccaacggc tactatcaca aatcctcatc aagctgacgc aagccctaag    1320
aaatga                                                               1326
```

<210> SEQ ID NO 6
<211> LENGTH: 441
<212> TYPE: PRT
<213> ORGANISM: Saccharomyces cerevisiae

<400> SEQUENCE: 6

```
Met Ser Ser Thr Ile Phe Tyr Arg Phe Lys Ser Gln Arg Asn Thr Ser
1               5                   10                  15

Arg Ile Leu Phe Asp Gly Thr Gly Leu Thr Val Phe Asp Leu Lys Arg
            20                  25                  30

Glu Ile Ile Gln Glu Asn Lys Leu Gly Asp Gly Thr Asp Phe Gln Leu
        35                  40                  45

Lys Ile Tyr Asn Pro Asp Thr Glu Glu Glu Tyr Asp Asp Asp Ala Phe
    50                  55                  60

Val Ile Pro Arg Ser Thr Ser Val Ile Val Lys Arg Ser Pro Ala Ile
65                  70                  75                  80

Lys Ser Phe Ser Val His Ser Arg Leu Lys Gly Asn Val Gly Ala Ala
                85                  90                  95

Ala Leu Gly Asn Ala Thr Arg Tyr Val Thr Gly Arg Pro Arg Val Leu
            100                 105                 110

Gln Lys Arg Gln His Thr Ala Thr Thr Thr Ala Asn Val Ser Gly Thr
        115                 120                 125

Thr Glu Glu Glu Arg Ile Ala Ser Met Phe Ala Thr Gln Glu Asn Gln
    130                 135                 140

Trp Glu Gln Thr Gln Glu Glu Met Ser Ala Ala Thr Pro Val Phe Phe
145                 150                 155                 160

Lys Ser Gln Thr Asn Lys Asn Ser Ala Gln Glu Asn Glu Gly Pro Pro
                165                 170                 175

Pro Pro Gly Tyr Met Cys Tyr Arg Cys Gly Gly Arg Asp His Trp Ile
            180                 185                 190
```

-continued

Lys Asn Cys Pro Thr Asn Ser Asp Pro Asn Phe Glu Gly Lys Arg Ile
            195                 200                 205

Arg Arg Thr Thr Gly Ile Pro Lys Lys Phe Leu Lys Ser Ile Glu Ile
210                 215                 220

Asp Pro Glu Thr Met Thr Pro Glu Glu Met Ala Gln Arg Lys Ile Met
225                 230                 235                 240

Ile Thr Asp Glu Gly Lys Phe Val Gln Val Glu Asp Lys Gln Ser
            245                 250                 255

Trp Glu Asp Tyr Gln Arg Lys Arg Glu Asn Arg Gln Ile Asp Gly Asp
            260                 265                 270

Glu Thr Ile Trp Arg Lys Gly His Phe Lys Asp Leu Pro Asp Leu
            275                 280                 285

Lys Cys Pro Leu Thr Gly Gly Leu Leu Arg Gln Pro Val Lys Thr Ser
            290                 295                 300

Lys Cys Cys Asn Ile Asp Phe Ser Lys Glu Ala Leu Glu Asn Ala Leu
305                 310                 315                 320

Val Glu Ser Asp Phe Val Cys Pro Asn Cys Glu Thr Arg Asp Ile Leu
            325                 330                 335

Leu Asp Ser Leu Val Pro Asp Gln Asp Lys Glu Lys Glu Val Glu Thr
            340                 345                 350

Phe Leu Lys Lys Gln Glu Glu Leu His Gly Ser Ser Lys Asp Gly Asn
            355                 360                 365

Gln Pro Glu Thr Lys Lys Met Lys Leu Met Asp Pro Thr Gly Thr Ala
            370                 375                 380

Gly Leu Asn Asn Asn Thr Ser Leu Pro Thr Ser Val Asn Asn Gly Gly
385                 390                 395                 400

Thr Pro Val Pro Pro Val Pro Leu Pro Phe Gly Ile Pro Phe Pro
            405                 410                 415

Met Phe Pro Met Pro Phe Met Pro Thr Ala Thr Ile Thr Asn Pro
            420                 425                 430

His Gln Ala Asp Ala Ser Pro Lys Lys
            435                 440

<210> SEQ ID NO 7
<211> LENGTH: 35
<212> TYPE: DNA
<213> ORGANISM: Artificial Sequence
<220> FEATURE:
<223> OTHER INFORMATION: Synthetic Primer

<400> SEQUENCE: 7
cggaattcca tatggctgtc atatactata agttc                              35

<210> SEQ ID NO 8
<211> LENGTH: 36
<212> TYPE: DNA
<213> ORGANISM: Artificial Sequence
<220> FEATURE:
<223> OTHER INFORMATION: Synthetic Primer

<400> SEQUENCE: 8
tttataatgc ggccgctcac ttttgattat tggtcg                             36

<210> SEQ ID NO 9
<211> LENGTH: 30
<212> TYPE: DNA
<213> ORGANISM: Artificial Sequence
<220> FEATURE:
<223> OTHER INFORMATION: Synthetic Primer

```
<400> SEQUENCE: 9
cccaagctta tgagtagcac gatattttac                                     30

<210> SEQ ID NO 10
<211> LENGTH: 30
<212> TYPE: DNA
<213> ORGANISM: Artificial Sequence
<220> FEATURE:
<223> OTHER INFORMATION: Synthetic Primer

<400> SEQUENCE: 10
atcaagcttt catttcttag ggcttgcgtc                                     30

<210> SEQ ID NO 11
<211> LENGTH: 33
<212> TYPE: DNA
<213> ORGANISM: Artificial Sequence
<220> FEATURE:
<223> OTHER INFORMATION: Synthetic Primer

<400> SEQUENCE: 11
ctcaagctta tgtcgtcagt cgtctactat aag                                 33

<210> SEQ ID NO 12
<211> LENGTH: 33
<212> TYPE: DNA
<213> ORGANISM: Artificial Sequence
<220> FEATURE:
<223> OTHER INFORMATION: Synthetic Primer

<400> SEQUENCE: 12
gggaagcttc taattcttct tctggttatt gac                                 33

<210> SEQ ID NO 13
<211> LENGTH: 30
<212> TYPE: DNA
<213> ORGANISM: Artificial Sequence
<220> FEATURE:
<223> OTHER INFORMATION: Synthetic Primer

<400> SEQUENCE: 13
acggagctcg gtagattagt aaaggaaatc                                     30

<210> SEQ ID NO 14
<211> LENGTH: 30
<212> TYPE: DNA
<213> ORGANISM: Artificial Sequence
<220> FEATURE:
<223> OTHER INFORMATION: Synthetic Primer

<400> SEQUENCE: 14
tatgagctct agtgatcgtt aaaggtgacc                                     30
```